(12) United States Patent
Linden

(10) Patent No.: US 12,372,263 B2
(45) Date of Patent: Jul. 29, 2025

(54) SYSTEM AND METHOD FOR THE MITIGATION OF RISK OF EXPOSURE TO CONTAMINANTS AND PROVIDING INFORMATION THEREOF

(71) Applicant: JOHNSON, LEVINSON, RAGAN, DAVILA, INC., West Palm Beach, FL (US)

(72) Inventor: Michael Patrick Linden, West Palm Beach, FL (US)

(*) Notice: Subject to any disclaimer, the term of this patent is extended or adjusted under 35 U.S.C. 154(b) by 580 days.

(21) Appl. No.: 17/707,551

(22) Filed: Mar. 29, 2022

(65) Prior Publication Data
US 2022/0307715 A1    Sep. 29, 2022

Related U.S. Application Data

(60) Provisional application No. 63/167,146, filed on Mar. 29, 2021.

(51) Int. Cl.
*F24F 11/52* (2018.01)
*A61L 9/20* (2006.01)
(Continued)

(52) U.S. Cl.
CPC .............. *F24F 11/52* (2018.01); *A61L 9/20* (2013.01); *B01D 46/0028* (2013.01);
(Continued)

(58) Field of Classification Search
CPC .... F24F 11/52; F24F 8/22; F24F 8/108; F24F 3/16; F24F 2110/20; F24F 2110/64;
(Continued)

(56) References Cited

U.S. PATENT DOCUMENTS 4,730,551 A * 3/1988 Peludat ............... F24F 13/068
454/236
5,042,997 A    8/1991 Rhodes
(Continued)

FOREIGN PATENT DOCUMENTS

KR    20200056141 A * 5/2022

*Primary Examiner* — Qianping He
(74) *Attorney, Agent, or Firm* — Derek Fahey; The Plus IP Firm, PLLC

(57) ABSTRACT

Disclosed is a method and system for the mitigation of risk of exposure to contaminants and providing information thereof. The method and system thereby follow the National Institute for Occupational Safety and Health (NIOSH) Hierarchy of Controls to implement a method and system to optimize safety guidelines and increase mitigation effectiveness. The method includes providing or using an existing air moving unit, mounting sensors for the continuous measurement of contaminants, flushing the enclosed area prior to and after occupancy for a specific time, filtering, diluting the enclosed area during occupancy, pressurizing for contamination control, maintaining humidity between 40% and 60%, providing ultraviolet germicidal irradiation to destroy and deactivate nuclear material in contaminants, cleaning, adjusting operational parameters between energy conservation mode and pandemic mode, and providing a display having information thereof about the enclosed area including the attributes and characteristics continuously monitored by sensors.

3 Claims, 17 Drawing Sheets

(51) Int. Cl.
*B01D 46/00* (2022.01)
*B01D 46/44* (2006.01)
*B01D 46/46* (2006.01)
*F24F 3/16* (2021.01)
*F24F 8/108* (2021.01)
*F24F 8/22* (2021.01)
*F24F 110/10* (2018.01)
*F24F 110/20* (2018.01)
*F24F 110/64* (2018.01)

(52) U.S. Cl.
CPC ....... *B01D 46/0049* (2013.01); *B01D 46/442* (2013.01); *B01D 46/448* (2013.01); *B01D 46/46* (2013.01); *F24F 3/16* (2013.01); *F24F 8/108* (2021.01); *F24F 8/22* (2021.01); *A61L 2209/111* (2013.01); *A61L 2209/14* (2013.01); *A61L 2209/16* (2013.01); *B01D 2273/30* (2013.01); *B01D 2279/50* (2013.01); *B01D 2279/65* (2013.01); *F24F 2110/10* (2018.01); *F24F 2110/20* (2018.01); *F24F 2110/64* (2018.01)

(58) Field of Classification Search
CPC ........ F24F 2110/10; F24F 11/30; F24F 11/63; F24F 11/39; F24F 11/0001; F24F 11/61; F24F 2110/50; F24F 2011/0002; F24F 2140/00; A61L 9/20; B01D 46/0028; B01D 46/0049; B01D 46/442; B01D 46/448; B01D 46/46; B01D 2273/30; B01D 2279/50; B01D 2279/65; B01D 46/00; B01D 46/44; G01N 2001/021; G01N 33/0034; G01N 33/0075; G05B 23/0221
USPC .......................................................... 95/271
See application file for complete search history.

(56) References Cited

U.S. PATENT DOCUMENTS

| | | | |
|---|---|---|---|
| 5,292,280 | A | 3/1994 | Janu et al. |
| 7,151,264 | B2 | 12/2006 | Ehlers, Sr. |
| 7,302,313 | B2 | 11/2007 | Sharp et al. |
| 8,772,744 | B1 | 7/2014 | Liu |
| 9,080,784 | B2 | 7/2015 | Dean-Hendricks et al. |
| 9,285,802 | B2 | 3/2016 | Arensmeier |
| 9,964,470 | B2 | 5/2018 | Sharp |
| 2012/0323374 | A1* | 12/2012 | Dean-Hendricks ...... F24F 11/61 700/276 |
| 2015/0323427 | A1* | 11/2015 | Sharp .................. G01N 1/2273 73/863.23 |

* cited by examiner

SYSTEM AND METHOD FOR THE MITIGATION OF RISK OF EXPOSURE TO CONTAMINANTS AND PROVIDING INFORMATION THEREOF

CROSS-REFERENCE TO RELATED APPLICATIONS

This application claims the benefit of the filing date of U.S. Provisional Application Ser. No. 63/167,146 titled "A System and Method for Mitigation of risk of exposure to contaminants and providing information thereof" and filed Mar. 29, 2021, and the subject matter of which is incorporated herein by reference.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISC

Not applicable.

TECHNICAL FIELD

The present disclosure relates to the field of HVAC systems, and more specifically to the field of HVAC systems for mitigating risk of exposure to contaminants.

BACKGROUND

The quality of air in an office, residential, school, and industrial buildings can significantly affect the health and productivity of a given building's occupants. Epidemics of asthma allergies, SARS-CoV-2 ("COVID-19"), and other airborne pathogens or irritants have made indoor air quality a critical factor.

Therefore, for commercial residential and industrial buildings, providing a good ventilation system with air-purification device is a key to provide better indoor air quality and to save energy. Many advanced technologies related to air purification devices for removal of pollutants from indoor air have recently been developed. These air purification devices include removal of particulate and gaseous that may be installed in the ductwork of building having a heating, ventilation, and air conditioning ("HVAC") system to clean the air, or a kind of portable room air cleaners that can be used to clean the air in a single room or in specific areas. HVAC systems are a commonplace in residential and workplace buildings or other structures for the control the ambient temperature within said structures.

Presently the problem with current technology is that air quality measures do not follow the National Institute for Occupational Safety and Health (NIOSH) Hierarchy of Controls to mitigate hazards corresponding to the environment. To adequately control the quality of the air, continuous monitoring must take place to determine what remedial measures must occur to provide a clean working space. To meet the current demands for air quality, a variety of systems and individual methods must be performed, the execution of which can be costly and time consuming and the physical cleaning of surfaces using disinfectants does not remove the risk of exposure to contaminants that may be present in the air.

For example, air contaminants and pollution contribute to the spread of infectious diseases. Studies have shown that there is a significant relationship between air pollution and respiratory infections such as COVID-19 and influenza. Zhu, Yongjian, et. al. *Association between short-term exposure to air pollution and COVID-19 infection: Evidence from China*, SCIENCE OF THE TOTAL ENVIRONMENT 727 (20 Jul. 2020); Xu, X., et. al., *Air Pollution and COVID-19 mortality in the United States: Strengths and limitations of an ecological regression analysis*, SCIENCE ADVANCES 6, 45 (4 Nov. 2021).

A result, there exists a need for improvements over the prior art and more particularly for a more efficient way of mitigating the risk of exposure to contaminants and providing information thereof.

SUMMARY

A system and method for mitigation of risk of exposure to contaminants and providing information thereof is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope. In one embodiment, a method for the mitigation of risk of exposure to contaminants is disclosed. The method includes providing or using an existing air moving unit for moving air within an HVAC system. Then mounting sensors for continuously measuring contaminants, pressure flow, humidity, temperature, and other attributes of the enclosed area. Before and after the enclosed area is occupied by beings, (flushing) continuously introducing air within the enclosed area using the air moving unit for a specified time. Then, (filtering) filtering air moving into the enclosed area using at least MERV 14 filters within the air moving unit or return duct. While the enclosed area is occupied by beings, (diluting) continually introducing air within the enclosed area to allow an increased number of air changes over normal air changes every hour. Then, (pressurization) balancing compartments within the enclosed area to either positive, negative, or neutral pressurization for contamination controls. The method also includes (humidity) maintaining the humidity within the enclosed area between 40%-60% humidity using the HVAC system. To deactivate contaminants from air moving into the enclosed area, (UV germicidal irradiation) providing UV/sanitization lights mounted to a UV infection rack within at least one of a return air duct, a supply air duct, and an air moving unit. Additionally, (cleaning) cleaning surfaces within the enclosed area based on Global Biorisk Advisory Council (GBAC) standards. The method further includes (adjusting modes) adjusting operational parameters of the flushing, filtering, and diluting step above based on (i) reducing energy consumption or (ii) reducing the risk of contaminants within the enclosed area; and providing a display illustrating whether the operational parameters of the enclosed area are maintained within specified limits. Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the disclosure and together with the description, serve to explain the principles of the disclosed embodiments. The embodiments illustrated herein are presently preferred, it being understood, however, that the disclosure is not limited to the precise arrangements and instrumentalities shown, wherein.

DETAILED DESCRIPTION

Figure 1:
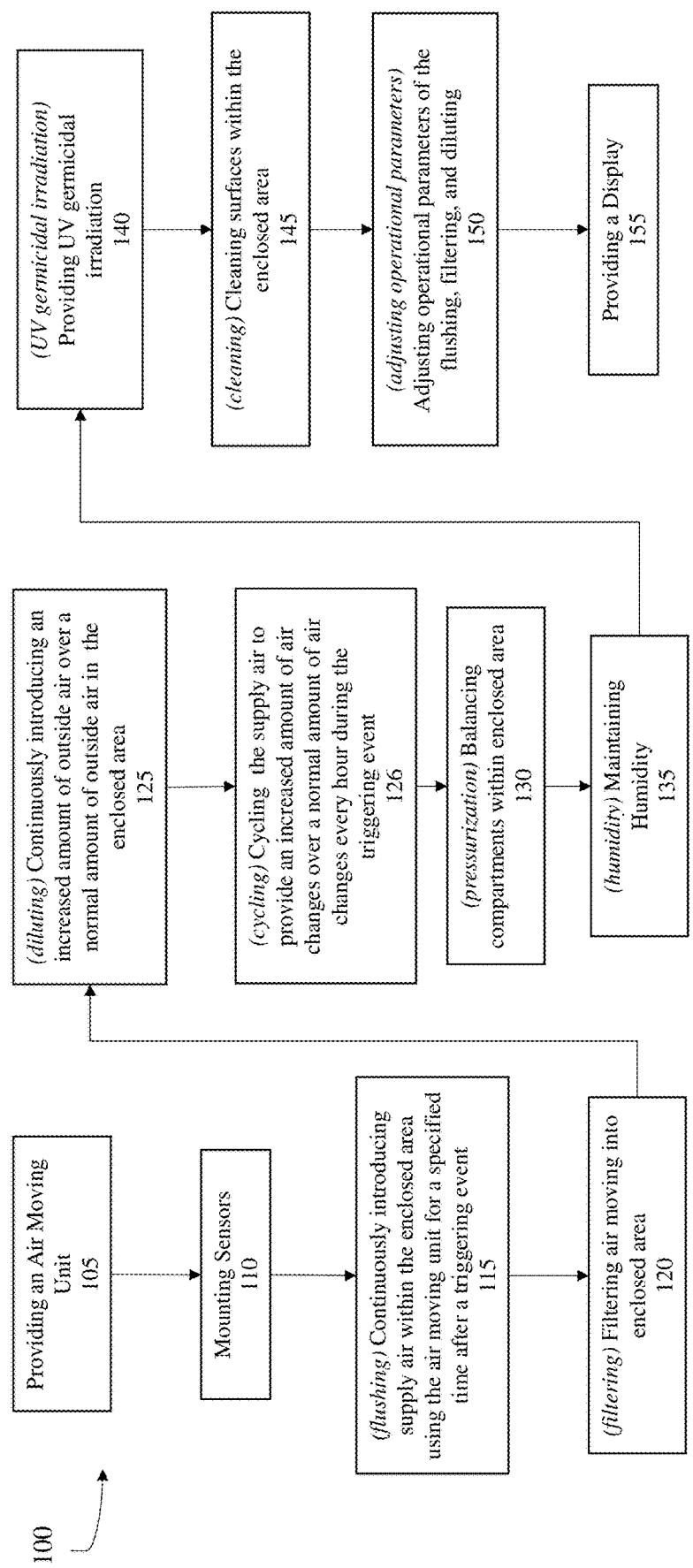
FIG. 1 is a block diagram of a method for the mitigation of risk of exposure to contaminants and providing information thereof, according to an example embodiment.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions, or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems with the prior art by providing a method and system consistent with the best practices identified by the National Institute for Occupational Safety and Health (NIOSH) Hierarchy of Controls, which serves as a guideline for hazard mitigation. This guideline states that mitigation measures should begin with source removal where feasible, and employ engineering controls such as modifying Heating, Ventilating, and Air Conditioning (HVAC) systems before the use of administrative controls such as policies and procedures, with the use of Personal Protective Equipment (PPE), such as wearing masks, being a last resort. In applying this approach, engineering controls that reduce the presence or concentration of contagions are given priority over engineering controls that only reduce contact with contagions that are present, such as plexiglass barriers. The disclosure implements the NIOSH hierarchy of controls, including elimination of the hazard, substitution, engineering controls, administrative controls, and personal protective equipment into a method of steps specifically designed to have synergistic effects increase the effectiveness of mitigation of risk of exposure.

For example, much in the same manner that good security requires a system of concenter perimeters with different methods for deterrence, detection, delay, and response before an intruder reaches the protected asset, an effective mitigation method requires the sequential application of techniques directed at eliminating, reducing the concentration, and destroying contagions before they can contact building occupants. This multi-layered system is strengthened by built-in redundancy to reduce the number of potential points of failure and incorporates continuous system performance monitoring for timely detection of malfunctions with real-time notification of building occupants as an additional safeguard that enables occupants to respond appropriately if the system does fail.

Referring now to the Figures, FIG. 1 is a block diagram of a method 100 for the mitigation of risk of exposure to airborne contaminants within an enclosed area and providing information thereof is shown, according to an example embodiment. The enclosed area is ideally a building. A compartment of the enclosed area is a room within the building, such as a classroom, office, patient room, etc. Other compartments are within the spirit and scope of this disclosure. Generally, a compartment is a separate room divided within the enclosed area, such as separated by a door to allow the compartment to be individually pressurized as compared to the rest of the enclosed area. The enclosed area may include at least one compartment. The method has synergistic effects to mitigate the risk of exposure to contaminants in the air, where the method includes providing 105 an air moving unit for moving supply air within an HVAC system. The air moving unit is an air handler, or air handling unit (AHU), that regulates and circulates air as part of an HVAC system. The HVAC system may be any exemplary HVAC system of the present technology. The supply air is the combination of return air from within the enclosed area and outside air. Outside air is air that comes from outside of the enclosed area. The method includes installing the air moving unit and retrofitting an existing air moving unit. Mounting 110 a plurality of sensors for continuously measuring a parameter value for each of a plurality of operational parameters of the enclosed area. The plurality of sensors may be temperature sensors, humidity sensors, and/or particulate counter/matter sensors; however, other types of sensors may be used and are within the spirit and scope of this disclosure. The parameter value is the value of the parameter that is monitored by the sensor; for example, the parameter value may be the number of particulate count, the percentage of humidity level, and/or the measurement of temperature of the enclosed area and/or the compartment. The operational parameters may include a particulate count, a humidity level, and a temperature of the enclosed area. The particulate count is the number of air particulate matter that is attached to a virus, bacteria, or other infectious diseases within the enclosed area and/or compartment. The humidity level is the percentage of humidity within the enclosed area and/or compartment. The sensors are mounted within the enclosed area and are configured to communicate with the air moving unit where the characteristics or attributes of the enclosed area are illustrated on a display.

The method 100 includes (flushing) flushing existing air within the enclosed area by continuously introducing 115 the supply air within the enclosed area using the air moving unit for a specified time after a triggering event. Existing air is the air that occupies the enclosed area. The specified amount of time may be enough time to allow an increased number of air changes. In certain embodiments, the specified amount of time is at least an hour. The triggering event may occur when the enclosed area is occupied by at least one being. In other embodiments, the triggering event may be when a foreign substance, such as a dangerous particulate, virus and/or bacteria, is introduced into the enclosed area. Moreover, other triggering events may be such that cause the operational parameters to exceed the predetermined threshold, such as a rapid increase in at least one of the temperature, the humidity, and/or the particulate count within the compartment and/or the enclosed area. More specifically, the triggering event may be people entering the enclosed area or compartment that previously included no other people, such an employee getting to the office before their coworkers.

Another triggering event may be a teacher entering an empty classroom before school starts. As soon as a human being occupies the enclosed area, the air moving unit constantly flows the supply air into the enclosed area to flush out the existing air. Step 115 utilizing the Energy Management System (EMS), where air would be introduced into the systems several hours prior to occupancy of the enclosed area, such as a school for example, and several hours after the beings, such as students and staff for example, leave the enclosed area. Flushing "pre-cleans" the air within the enclosed area, allowing all beings to enter a "clean" building. Once the beings leave, the air moving units will continue to flush out contaminants for several hours or until the attributes or characteristics of the enclosed area reaches its respective safe ranges and a safe range within an overall net condition threshold of an overall net condition of the enclosed area.

(Filtering) Filtering 120 the supply air moving into the enclosed area using at least MERV 14 filters within the air moving unit or return duct. Typical filtration efficiencies are 60% while MERV 14 filters are 85% efficient. Step 120 includes filtering particulates that comprise at least one of a virus and a bacteria that is attached to moisture within the supply air using at least one filter within at least one of the air moving unit and a return duct, wherein the at least one filter is at least thirty percent efficient at removing the virus and the bacteria from the supply air. Step 120 may also include filtering contaminants within the air such as dust, pollen, microorganisms such as mold and archaea, and submicroscopic infectious agents that attach to air particulate matter such as SARS-CoV-2 (COVID-19) and influenza for example. Viruses, for example, attach to moisture droplets allowing it to be captured within the filter. The level of filtration will differ depending on the type of HVAC system. In other embodiments, MERV-14 filters provide the most efficient filter without modifications to the existing air moving units. MERV-14 filters are electrostatic air filters that multiple filtration layers that are made of a material that gives particulates a positive charge such that the particulates may attach to the rest of the layers of the filter. As more particulates are caught by the layers and bind together, a buildup of particulates becomes too large to permeate the filter.

(Diluting) Diluting 125 the supply air within the enclosed area by continuously introducing an increased amount of outside air over a normal amount of outside air in the enclosed area. The normal amount of outside air is the amount of air that an exemplary HVAC system would allow in a room or building. Generally, the acceptable amount of outside air depends on the recommended ventilation rate of all air flow within a room, the number of people in the room and the volume of the enclosed area. The recommended ventilation rate for outside air is 20 CFM (cubic feet per minute) per person. Therefore, to introduce the increased amount of outside air, the air moving must introduce an amount of outside air that allows the ventilation rate to exceed the recommended ventilation rate of outside air. For example, if a room is 1000 cubic feet and is occupied by 10 people, the amount of outside air in the room should be about 20 percent of total air to reach a ventilation rate of 20 CFM per person. Thus, the air moving unit must introduce the increased amount of outside air that exceeds 20 percent of the total air in the enclosed area. The increased amount of outside air dilutes the supply air in the room. Dilution is directly related to flushing and part of the EMS solution. Introducing air during dilution may typically include outside air such that the air is from the outside of the enclosed area. Dilution includes increasing the percentage of air for each air moving unit system.

(Cycling) Cycling 126 the supply air to provide an increased amount of air changes over a normal amount of air changes every hour during the triggering event. In other embodiments, the increased number of changes over normal air changes every hour is 3.0 over normal air changes. Air changes are the full replacement of existing air within the enclosed area. More specifically, air changes mean that all the air that was already in the enclosed area leaves the enclosed area and is replaced by new supply air. A normal amount of air changes per hour (ACH) depends on the volume of the enclosed area, local regulations and codes, and geographic location of the enclosed area. The system dilutes the supply air by providing an increased volume of outside air. For example, if a normal existing HVAC system cycles air at least 1.3-1.6 ACH, then the methods disclosed herein will provide an increased number of ACH by flushing the existing air, diluting the supply air, and cycling the air within the system. For example, if the supply air during a normal air change of an existing HVAC is comprised of 75% return air and 25% outside air, then the retrofitted system will dilute the air such that the supply air comprises, for example, 25% return air and 75% outside air. This may be achieved by evacuating the return air outside instead of reintroducing it within the system and/or introducing a greater volume of outside air compared to return air. For example, the former may be preferred if the room is contaminated such that a particulate count is above a predetermined threshold. That said, the methods disclosed herein may achieve an increased number of ACH. For example, if a standard HVAC system in Florida achieves on a normal average 1.3-1.6 ACH, then the methods disclosed herein enable the system to achieve 2-2.7 ACH. It is understood that the geographic location of the enclosed area is a limiting constraint on the achievable ACH. For example, because an enclosed area in Maine, for example, may increase from 1.9 ACH to over 3 ACH per hour because of the decreased humidity of the surrounding environment. The methods and systems described herein improve upon the prior art by providing an efficient system to achieve an increased number of ACH as compared to the normal amount of air changes. Other increased amounts of air changes per hour are within the spirit and scope of this disclosure.

The method 100 additionally includes (Pressurization) balancing 130 a compartment air pressure for at least one compartment within the enclosed area compartments within the enclosed area. The compartment air pressure is the level of air pressure within a compartment within the enclosed area. Balancing the compartment air pressure includes configuring the compartment to one of positive pressurization, negative pressurization, or neutral pressurization to control contaminants. The enclosed area will be balanced to either positive, negative, or neutral pressurization to allow for contamination control of compartments. An overwhelming majority of spaces within the enclosed area should be neutral. This control of relative pressure reduces the potential for contamination transferring with the enclosed area such as between ventilated rooms. Negative pressurization causes the pressure in the compartment to be less than the pressure outside the compartment. Negative pressurization causes the existing air to move out of the compartment and allows existing air to escape the compartment through the exhaust and return air duct such that contaminants and particulates are able to leave the compartment to be released outside or filtered. Positive pressurization causes the pressure in the compartment to be more than the pressure outside the compartment. Positive pressurization causes supply air to flow into the compartment to dilute the existing air. Neutral pressurization causes the pressure in the compartment to be the same as the pressure outside the compartment. For example, the system may negatively pressurize a room that is contaminated with a high particulate count and/or is not within the safe range. This will prevent the door to the enclosed area from opening until the enclosed area and/or compartment has its operational parameters below the predetermined threshold. Similarly, high pressurization may be used to promote dilution of the air within the enclosed area or compartment and/or to efficiently flush the air after a triggering event (i.e., when the enclosed area is no longer occupied by persons). An example of this may be when a school is closed after the children and teachers have been dismissed for the evening. The pressurization may be high to flush the system to provide a safe environment until the next triggering event. A normal pressurization may be during the triggering event when the enclosed area is occupied by people and/or the enclosed and/or its compartments are within a safe range. In embodiments with multiple compartments within the enclosed area, it is understood that an unsafe compartment may be negatively pressurized while the remaining portions of the enclosed area are neutral and/or positively pressurized. Similarly, if the enclosed area is contaminated, the system may positively pressurize certain compartments that are within the safe range to prevents airborne pathogens from entering the room to avoid the air becoming contaminated. Likewise, a negative pressurization of a compartment and/or the enclosed area prevents airborne pathogens from leaving the compartment and/or enclosed are to avoid contaminating other safe areas.

(Humidity) Maintaining 135 the humidity level of the enclosed area within a predetermined humidity range. The predetermined humidity range within the enclosed area is between 40%-60% humidity using the HVAC system. A being's body's natural defense mechanisms works most effectively when the humidity within the enclosed area is between 40-60%. This humidity range is achieved via the Building Automatial Systems (BAS).

(UV Germicidal Irradiation) Providing 140 UV/sanitization lights mounted to a UV infection rack within at least one of a return air duct, a supply air duct, and an air moving unit for deactivating contaminants from air moving into the enclosed area. A UV infection rack has a plurality of ultraviolet lights. The plurality of ultraviolet lights allows for an increased contact time with the moving air within the air moving unit. The UV infection rack and ultraviolet lights destroy, damage, and deactivate nuclear material within viruses and bacteria using the frequency of the ultraviolet light thereby decreasing the risk of exposure to a harmful air contaminant. The plurality of ultraviolet lights also destroys, damages, and deactivates nuclear material within viruses and bacteria that may be present on the surfaces within the air moving unit and on the surface of the at least one coil. The supply air duct is an opening that releases the supply air. The return air duct is an opening that receives return air.

(Cleaning) Cleaning 145 surfaces within the enclosed area based on Global Biorisk Advisory Council (GBAC) standards. This step includes training staff to physically scrub, clean, or disinfect the enclosed area if the attributes or characteristics of the enclosed area are within the upper limits of the safe range as indicated by a yellow indicator on the display or exceeding the upper limits of the safe range as indicated by a red indicator on the display.

(Adjusting Modes) Adjusting 150 operational parameters of the flushing, filtering, and diluting step above based on (i) reducing energy consumption or (ii) reducing the risk of contaminants within the enclosed area. The system will have at least two modes of operation. The normal sequence, or default, operation will be an "Energy Conservation Mode". The Energy Conservation Mode promotes energy savings measures such as reduced outside air and optimization of start/stop times of chillers and AHUs. The second mode, "Pandemic Mode" will turn on the mitigation system for the mitigation of risk of exposure to contaminants. Adjusting operational parameters includes engaging the system to implement step 115, 120, and 125.

The method 100 further includes providing a display illustrating if the parameter value of each of the plurality of operational parameters are maintained below a predetermined threshold. The predetermined threshold depends on the desired levels of particulate, humidity, and temperature. More specifically, the levels of particulate count, humidity, and temperature should not exceed their predetermined thresholds; otherwise, people in the enclosed area would be at risk. The display has indicators where there are visual representations of the attributes or characteristics of the enclosed area as continuously monitored by the sensors. The display may also include an overall net condition of the enclosed area, the status of specific attributes or characteristics, and a depiction of the enclosed area. The display includes at least one of a first indicator, a second indicator, a second indicator, and a fourth indicator. The first indicator indicates the particulate count of the enclosed area relative to a particulate count predetermined threshold. The particulate count predetermined threshold is the limit of particulates that the enclosed area may have. The second indicator indicates the temperature of the enclosed area relative to a temperature predetermined threshold. The temperature predetermined threshold is the limit of temperature levels that the enclosed area may have. The third indicator indicates the humidity of the enclosed area relative to a humidity predetermined threshold. The humidity predetermined threshold is the limit of humidity levels that the enclosed area may have. The fourth indicator indicates the overall net condition of the enclosed area relative to an overall net condition predetermined threshold. The overall net condition of the enclosed area depends on the levels of the operational parameters and represents whether any of operational parameters is close to reaching or already exceeded their respective thresholds. The overall net condition threshold is the limit that the overall net condition may be. The display further includes a green indicator indicating that the enclosed area is below at least one of the particulate count predetermined threshold, the temperature predetermined threshold, the humidity predetermined threshold, and the overall net condition predetermined threshold. The display also includes yellow indicator that indicates the enclosed area is proximate to an upper limit of at least one of the particulate count predetermined threshold, the temperature predetermined threshold, the humidity predetermined threshold, and the overall net condition predetermined threshold. The red indicator displays when the enclosed area exceeds the upper limit of at least one of the particulate count predetermined threshold, the temperature predetermined threshold, the humidity predetermined threshold, and the overall net condition predetermined threshold.

Figure 2:
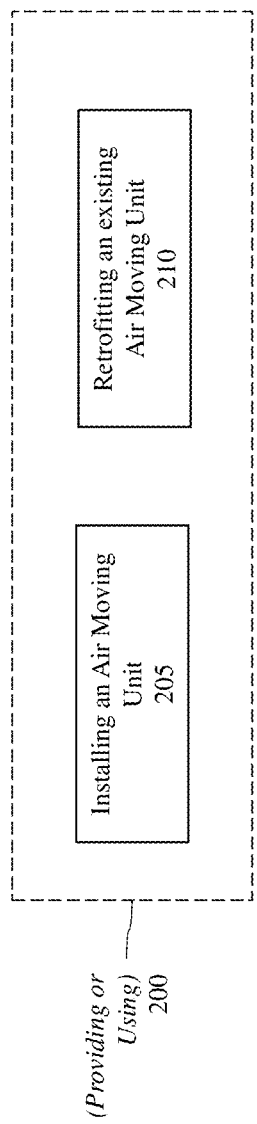
FIG. 2 is a block diagram of providing or using an existing air moving unit for moving air within an HVAC system, according to an example embodiment.

Referring now to FIG. 2, a block diagram of providing or using 105 an existing air moving unit for moving air within an HVAC system is shown, according to an example embodiment. Providing or using 105 may further include providing or using 200 an existing air moving unit may further include at least one of installing 205 an air moving unit and retrofitting 210 an existing air moving unit. In an example embodiment, an enclosed area may require the installation of an air moving unit having the technologies consistent with this disclosure. Thereto providing said air moving unit configured to incorporate the method 100. Likewise, an enclosed system may already include an air moving unit where the air moving unit may need to be retrofitted with technology consistent with this disclosure. For example, an existing air moving unit may need to be retrofitted with a UV infection rack or it may need to be configured to implement the method 100 using a processor. The air moving unit may further need to be configured to providing a display where such display may illustrate the overall net conditions of the enclosed area.

Figure 3:
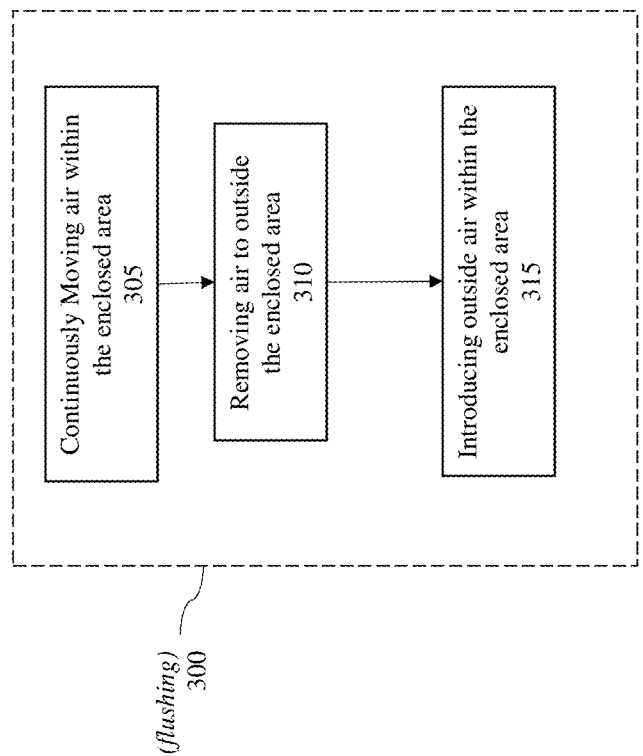
FIG. 3 is a block diagram of flushing by continuously introducing air within the enclosed area using the air moving unit for a specified time prior to and after the enclosed area is occupied by beings, according to an example embodiment.

Referring now to FIG. 3, a block diagram of flushing 115 by continuously introducing air within the enclosed area using the air moving unit for a specified time prior to and after the enclosed area is occupied by beings is shown, according to an example embodiment. Flushing 115 may further encompass flushing 300 including continuously moving air 305 within the enclosed area using the air moving unit, removing 310 return air from within the enclosed area where the return air is moved outside the enclosed area, and introducing 315 the supply air having the increased amount of outside air over the normal amount of outside air within the enclosed area. Continuously moving air 305 may include turning on the blower of the air moving unit or fans within the enclosed area where air is circulating within the enclosed area where the air within the enclosed area is not stagnant. Removing 310 return air to outside the enclosed container may include opening vents or the return air duct where new air enters the enclosed area. In a sterile environment, opening vents where air can flow through air the return air duct will allow the air that was in the area to enter the air moving unit. From the air moving unit, the air can be filtered where the contaminants from the air are removed as the air passes through a filter. Then, the contaminants will be destroyed as the air passes through a UV infection rack where ultraviolet germicidal irradiation is used to kill or inactivate microorganisms by destroying nucleic acids and disrupting the DNA, rendering the microorganisms unable to perform vital cellular functions. Removing 310 may further include opening windows where emergent remedial measures must be undertaken to evacuate the contaminated air within the enclosed area. Introducing 315 air within the enclosed area may include, for example, introducing air where the air has passed through the filter and over the UV infection rack. Introducing 315 air into the enclosed system using the air moving unit where air travels from the air moving unit to the enclosed area through a series of supply air ducts. Continuously introducing air also includes introducing air that originated from outside of the system and the enclosed environment such that the air newly enters the air moving unit. The air may also be recycled such that the air from the enclosed room returned to the air moving unit through the return air ducts.

Figure 4:
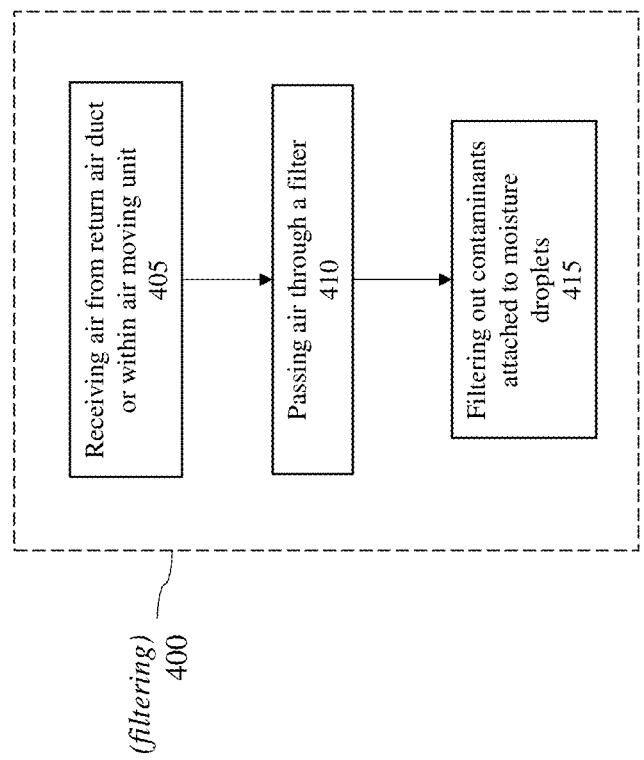
FIG. 4 is a block diagram of filtering air moving into the enclosed area using at least MERV 14 filters within the air moving unit or return duct, according to an example embodiment.

Referring now to FIG. 4, a block diagram of filtering 120 air moving into the enclosed area using at least MERV 14 filters within the air moving unit or return duct is shown, according to an example embodiment. Filtering 120 may further encompass filtering 400 including receiving 405 air from at least one of the return air duct or within the air moving unit. In one embodiment, a filter is placed within the return air ducts. In another embodiment, a filter is placed between the return air duct and the air moving unit. In other embodiments, a filter may be placed within the air moving unit. Further embodiments may include a filter within a supply air duct or between an air moving unit and a supply air duct. Other embodiments pertaining to the location of a filter are foreseen within the spirt and scope of this disclosure. In other embodiments, multiple filters may be used. Filtering 400 may further include passing 410 air through a filter where moving the air through a filter causes the filter to trap particles and contaminants of particular microns with a particular efficiency within the spirit and scope of this disclosure. Filtering may further include filtering 415 out contaminants within the air. Such contaminants may be attached to moisture droplets where contaminants of microns smaller than the efficient range of the filter are attached to moisture droplets in the air having a micron size within the filters range. Therefore, the contaminants may be trapped within the filter or filtered out of the air. Filtering 400 includes filtering viruses and bacteria attached to moisture droplets within the air using at least one filter where the at least one filter is at least thirty percent (30%) efficient at removing viruses and bacteria from the air.

Figure 5:
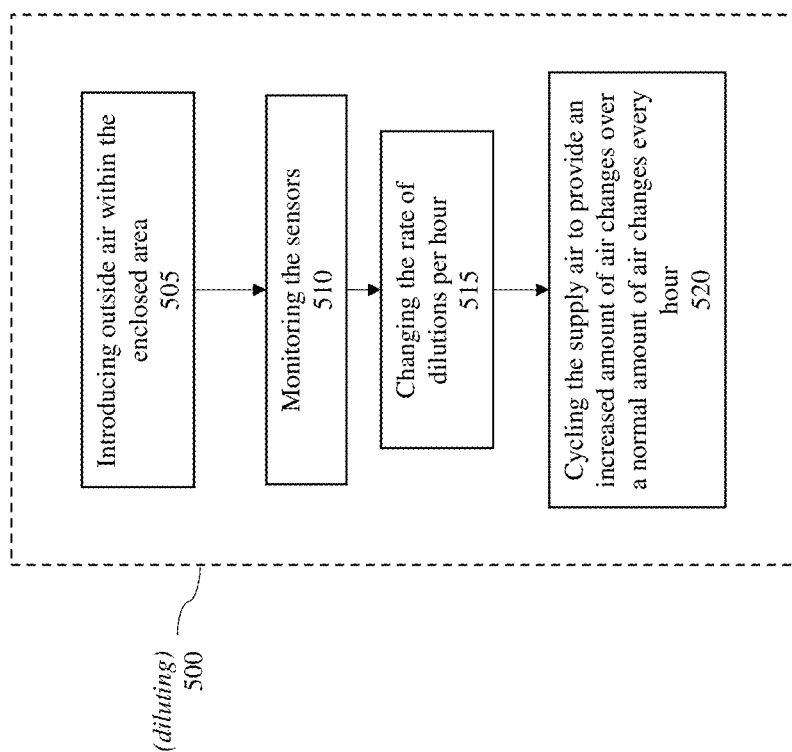
FIG. 5 is a block diagram of diluting by continually introducing air within the enclosed area to allow an increased number of air changes over normal air changes every hour when the enclosed area is occupied by beings, according to an example embodiment.

Referring now to FIG. 5, a block diagram of diluting 125 by continually introducing air within the enclosed area to allow an increased number of air changes over normal air changes every hour when the enclosed area is occupied by beings is shown, according to an example embodiment. Diluting 125 may further encompass diluting 500 including continuously introducing 505 air within the enclosed area at least two times every hour when the enclosed area is occupied by beings. Introducing 505 air within the enclosed area may include, for example, introducing air where the air has passed through the filter and over the UV infection rack. Introducing 315 air into the enclosed system using the air moving unit where air travels from the air moving unit to the enclosed area through a series of supply air ducts. Continuously introducing air also includes introducing air that originated from outside of the system and the enclosed environment such that the air newly enters the air moving unit. The air may also be recycled such that the air from the enclosed room returned to the air moving unit through the return air ducts.

Diluting 500 may also include continuously monitoring 510 a sensor within the enclosed area where if a sensor exceeds a predetermined threshold, then changing 515 the rate of dilutions per hour. Diluting 500 may also include continuously monitoring outside air where outside air is introduced if it is within a predetermined threshold of a safe condition. Outside air must be continuously monitored such that unclean or contaminated air is not introduced within the enclosed environment. The condition of the outside air and the air volume of the enclosed area affect the dilution rate per hour of continuously introducing air within the enclosed environment. Diluting 500 occurs while the enclosed area is occupied by beings where air is continuously introduced to reduce the exposure and risk to contaminants. The introduced air has been flushed and filtered within the spirt and scope of this disclosure. Changing 515 the rate of dilutions may include increasing the rate of dilutions or decreasing the rate of dilutions per hour to maintain optimal overall net conditions of the enclosed area. In one embodiment, one dilution per hour is required. In another embodiment, at least two dilutions per hour may be required. In other embodiments, more dilutions per hour may be required. The dilution rate per hour may depend on the characteristics of the enclosed area including, volume of the enclosed area, ceiling height of the enclosed area, number of beings within the enclosed area, ventilation of the enclosed area, and other characteristics that may affect the air or risk of exposure to contaminants. If the risk of exposure to contaminants is high, changing 515 the rate of dilutions where the rate of dilutions increases per hour. If, for example, the risk of exposure to contaminants decreases after the dilutions and overall net conditions are satisfied, then decreasing the rate of dilutions per hour. Decreasing the rate of dilutions per hour may result in energy efficiency and cost savings when a high rate of dilution is not necessary to treat an enclosed area. Cycling 520 the supply air may include increasing the amount of air changes over a normal amount of air changes every hour during the triggering event. Air changes fully replace existing air with supply air within the enclosed area.

Figure 6:
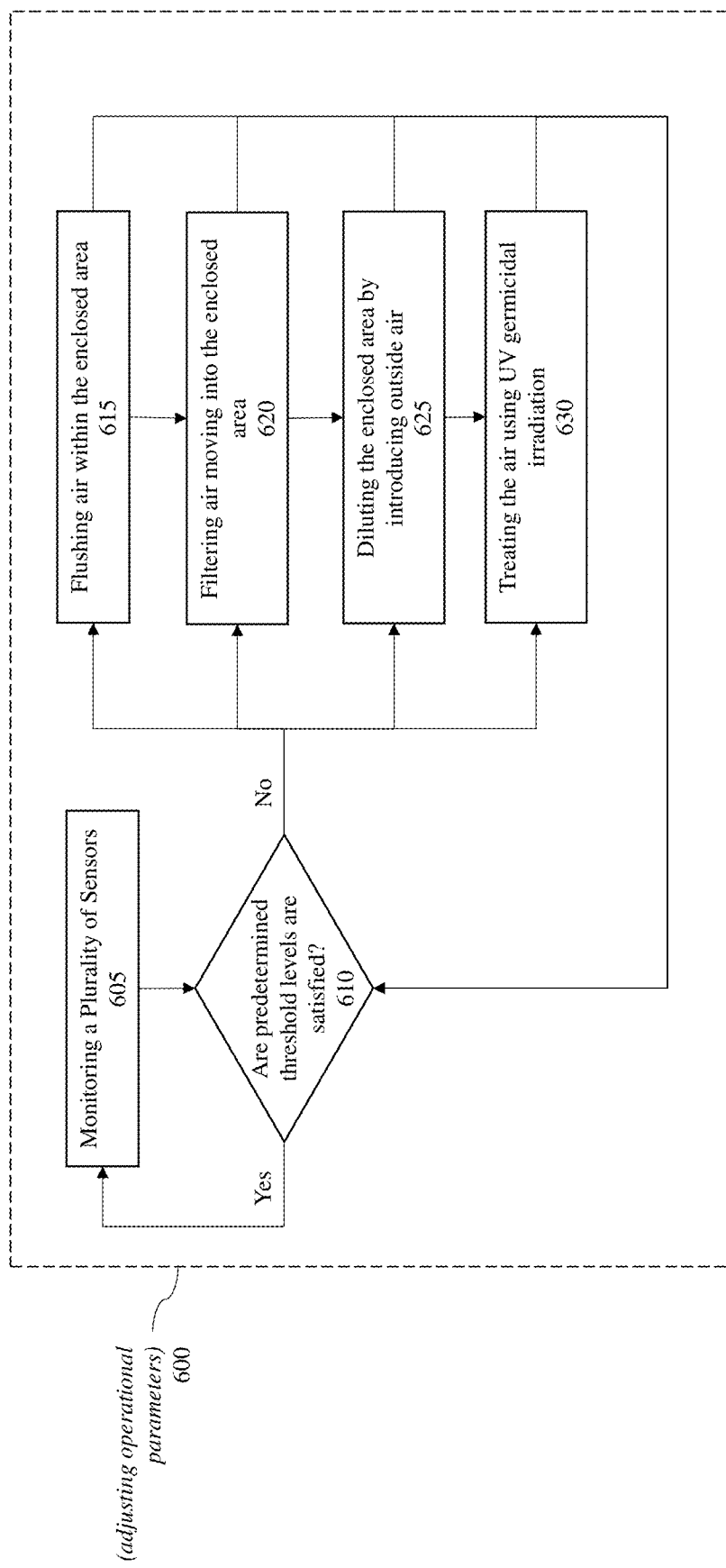
FIG. 6 is a block diagram of adjusting operational parameters of the flushing, filtering, and diluting step above based on (i) reducing energy consumption or (ii) reducing the risk of contaminants within the enclosed area, according to an example embodiment.

Referring now to FIG. 6, a block diagram of adjusting operational parameters 150 of the flushing, filtering, and diluting step above based on (i) reducing energy consumption or (ii) reducing the risk of contaminants within the enclosed area is shown, according to an example embodiment. Adjusting operational parameters 150 may further encompass adjusting operational parameters 600 include continuously monitoring 605 a plurality of sensors, where the sensors may be configured to detect and measure changes in environmental conditions such as the condition of the enclosed area including characteristics such as humidity, temperature, and particulate count and the condition of the outside air, for example. The sensor converts the physical characteristic of the enclosed environment into a measurable analog voltage or digital voltage converted into at least one of a display and transmitted as a first signal to a processor configured to adjust the operational parameters of the system for the mitigation of risk of exposure to contaminants. The processor is configured to receive a first signal. In an example embodiment, the monitoring 605 includes monitoring a plurality of sensors. The processor will determine 610 whether the predetermined threshold levels of the sensor or plurality of sensors are satisfied. The predetermined threshold level may be a threshold level for the specific measured parameter or the threshold level for the overall net condition of the enclosed environment. If the predetermined threshold levels are satisfied, then continuously monitoring 605 the sensor or plurality of sensors within the enclosed area. If the predetermined threshold levels are not satisfied, then performing at least one of flushing 615 the air within the enclosed area where continuously introducing air within the enclosed area using the air moving unit for a specified time prior to and after the enclosed area is occupied by beings; filtering 620 air moving into the enclosed area using at least MERV 14 filters within the air moving unit or supply air duct; diluting 625 the enclosed area where introducing air within the enclosed area to allow increased air changes every hour when the enclosed area is occupied by beings; and, treating 630 the air within the enclosed area using ultraviolet lights mounted to a UV infection rack within the system.

Figure 7:
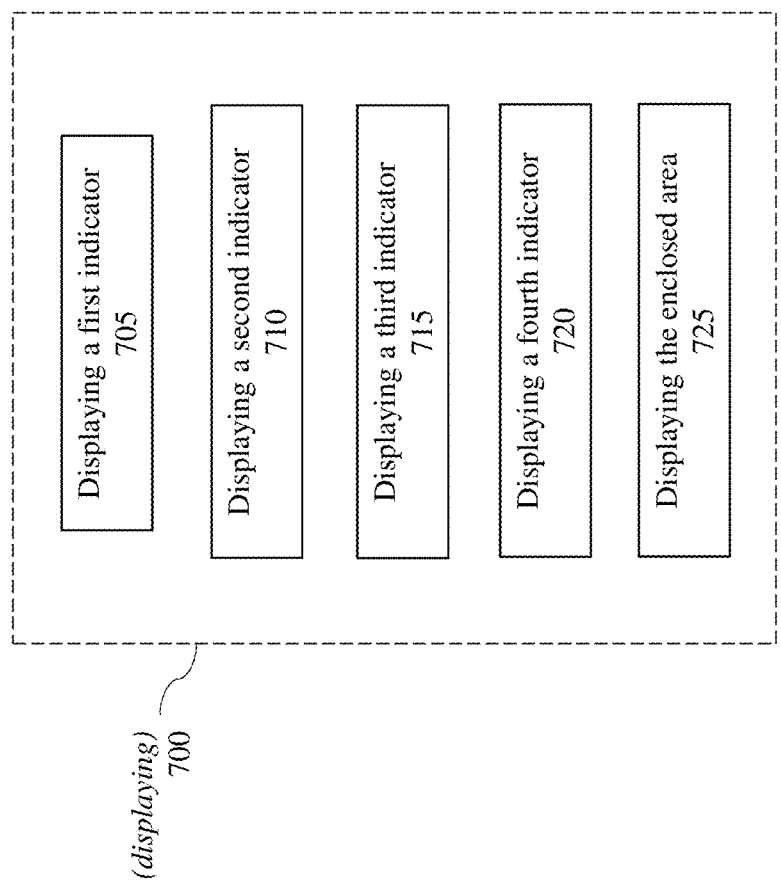
FIG. 7 is a block diagram of displaying by providing a display illustrating whether the characteristics of the enclosed area are maintained within specified limits, according to an example embodiment.

Referring now to FIG. 7, a block diagram of providing 140 a display illustrating whether the characteristics of the enclosed area are maintained within specified limits is shown, according to an example embodiment. Providing 135 may encompass displaying 700 at least one of displaying a first indicator 705, displaying a second indicator 710, displaying a third indicator 715, displaying a fourth indicator 720, and displaying the enclosed area 725. Displaying a first indicator 705 indicates the particulate count of the enclosed area relative to the particulate count predetermined threshold. Displaying a second indicator 710 indicates the temperature of the enclosed area relative to the temperature predetermined threshold. Displaying a third indicator 715 indicates the humidity of the enclosed area relative to the humidity predetermined threshold. Displaying a fourth indicator 720 indicates the overall net condition of the enclosed area relative to the overall net condition predetermined threshold. The overall net condition of the enclosed area measures the net impact of the first indicator, second indicator, and third indicator on the overall net condition of the enclosed area. The overall net condition is optimally within the safe range. Either of the first indicator exceeding the limits of the first range, the second indicator exceeding the limits of the second range, and the third indicator exceeding the limits of the third range may move the overall net condition of the enclosed area within the upper limits of the safe range or exceeding the upper limits of the safe range. Displaying the enclosed area 725 may include a graphical depiction of the enclosed area, for example, a blueprint of a building or a particular ventilated room. In one embodiment, the displaying the enclosed area 725 having at least one ventilated room. In another embodiment, displaying the enclosed area having a plurality of ventilated rooms. A ventilated room has a supply duct and a return duct to receive supply air and expel existing air.

Figure 8:
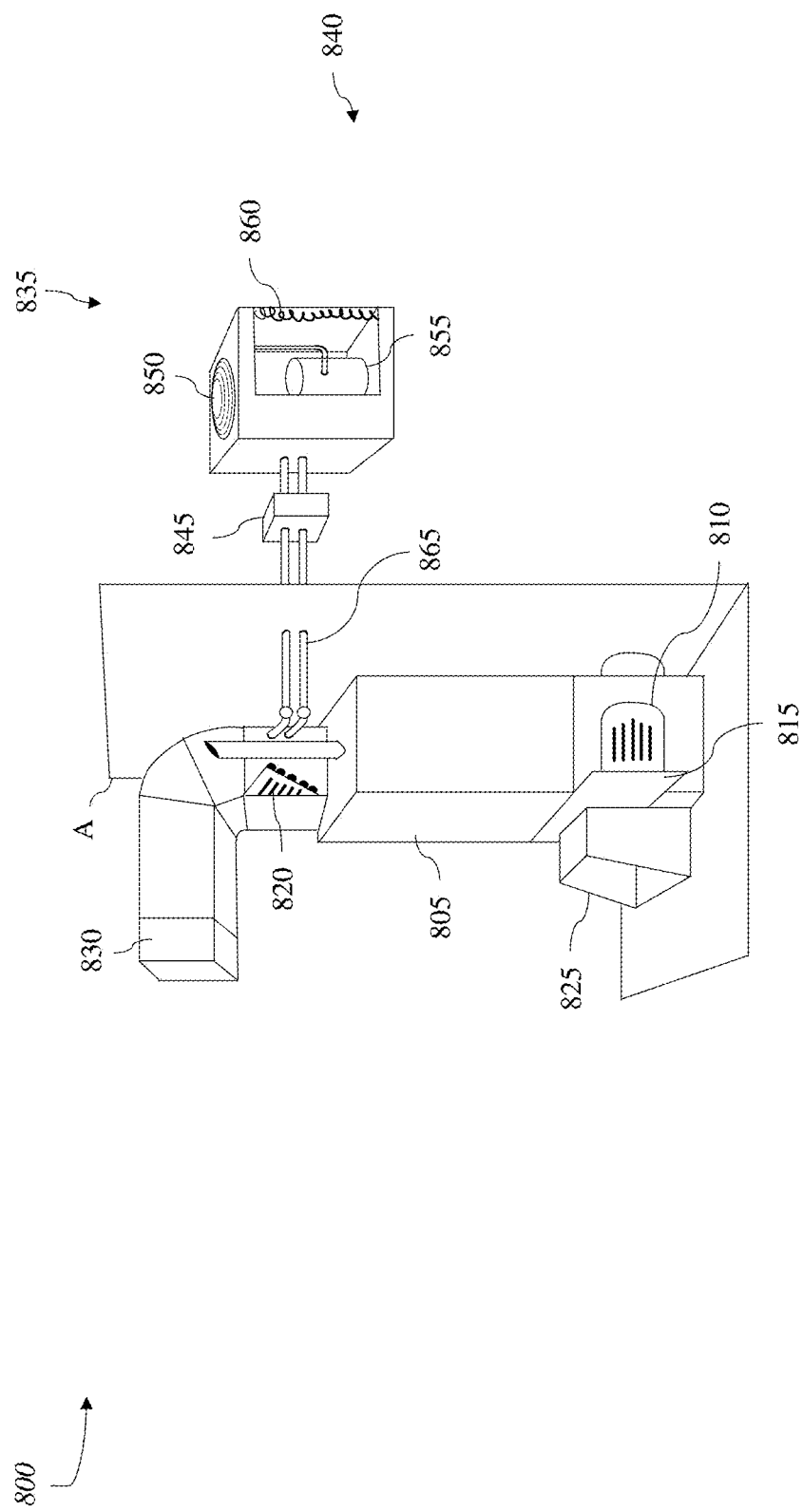
FIG. 8 is a diagram illustrating the components of a system for the mitigation of risk of exposure to contaminants and providing information thereof, according to an example embodiment.

Referring now to FIG. 8, a diagram illustrating the components of a system 800 for the mitigation of risk of exposure to contaminants and providing information thereof is shown, according to an example embodiment. The system including at least two or more of an air moving unit 805 where the air moving unit has a blower 810, at least one filter 815, and a coil 820. The system also includes at least one ventilated room where the at least one ventilated room includes a return air duct 825 operatively connected to the air moving unit. The system includes an supply air duct 830 operatively connected to the air moving unit and the at least one ventilated room. At least one first pump is operatively coupled to a boiler and the air moving unit. At least one second pump is operatively coupled to a cooling source 835. The first pump and second pump may be centrifugal pumps used for fluid transfer. Types of centrifugal pumps may include axial flow or volute pumps; however, other pumps may be used and are within the spirit and scope of this disclosure. The first pump allows for the heating of the supply air while the second pump allows for the cooling of the supply air. The system further includes a display illustrating whether the characteristics of the enclosed area are maintained within specified limits including at least one of displaying a first indicator having a particulate count of the enclosed area, where the particulate count within the enclosed area is within a first range. The system displays a second indicator having a temperature of the enclosed area, where the temperature of the enclosed area is within a second range. The system also displays a third indicator having a humidity of the enclosed area, where the humidity of the enclosed area is within a third range. The system further displays a fourth indicator having an overall net condition of the enclosed area, where the overall net condition of the enclosed area is within a safe range; The system displays the enclosed area, including the at least one ventilated room. In other embodiments, the system may include multiple air moving units.

(Air Mover Unit) The air moving unit has a blower, at least one filter, and a coil. The air moving unit may include moving units such as heating, ventilation, and air conditioning or HVAC units, having split-system air conditioning units such as, a central air conditioner, mounter air conditioner, ceiling air conditioners, or stand-alone air conditioner units such as portable air conditioners, window air conditioners, spot coolers, and floor mounted air conditioners. In some embodiments, the air moving unit may further include an air conditioner, an air handler, an air handling unit, a British thermal unit, a centrifugal fan.

(Filter) The system may include at least one filter where the filter is at least a MERV 14 efficiency. The Minimum Efficiency Reporting Values (MERV) is a filters ability to capture larger particles between 0.3 and 10 microns. In accordance with this disclosure, at least a MERV 14 filter is used where the particles between 0.3-1.0 microns are trapped within the filter at seventy-five percent (75%) to eighty-four (84%) efficiency, particles between 1.0-3.0 microns are trapped within the filter at ninety (90%) or greater efficiency. Better filters may be used, including MERV 15 and MERV 16 filters where particles of smaller microns are trapped at a higher percent efficiency. In other embodiments, high efficiency particulate air (HEPA) filters or high efficiency particular air filters may be used where the filter can remove at least ninety-nine-point ninety-seven percent (99.97%) of dust, pollen, mold, bacteria, and any airborne particles with a size of 0.3 microns. Various filters may be used of at least 30% efficiency. Ideally the system should operate with at least one filter being at least 60% efficiency. Because the system cycles supply air comprising return air and outside air, the system may include a filter in the return air duct to filter the return air, the air moving unit to filter the outside air and the return air, and/or the supply air duct.

(Blower and Coil) The blower includes a fan such as a centrifugal fan where the centrifugal fan is configured to move air throughout the system. The blower, as configured within the air moving unit is directed at the at least one coil where the at least one coil is configured to allow liquid or gases to travel through the coil either heating or cooling the at least one coil. As the blower moves the air past the coil, the air is either heated or cooled. The blower then moves the air through the supply air ducts where the air travels to the enclosed area and enters the at least one ventilated room. In one embodiment the at least one coil is an evaporator coil where the at least one evaporator coil holds chilled refrigerant that the compressor of the cooling source moves into it. The at least one coil works in conjunction with the condenser coil to dehumidify the air while maintaining the humidity within a specified range. In other embodiments, the at least one coil may include coils such as hot water coils, chilled water coils, and direct expansion coils.

(Boiler) The boiler is configured to heat water where the boiler expends energy as measured in British thermal units or British thermal units per hour to raise at least one pound of water by one degree Fahrenheit. When the system is heating the enclosed area, the heated liquid, such as hot water, flows through the at least one coil using a first pump where the at least one coil is a heating coil of the air moving unit to warm the air within the air moving unit.

(Cooling Source) The cooling source may further include at least one of a chilled water system and cooling tower where the cooling tower 840 includes a chiller 845, a fan 850, a compressor 855, a condenser coil 860, and refrigerant filled tubing 865. The cooling source includes chilled liquid such as water or refrigerant, where the chilled liquid is pumped to the at least one coil within the air moving unit. Where the cooling source is a cooling tower, the cooling tower having a compressor and a condenser coil work in conjunction with the at least one coil 820 of the air moving unit where the air moving unit and the cooling tower are operatively connected via the refrigerant filled tubing. Where the cooling source is a chilled water system, the chilled water system is operatively connected to the air moving unit where chilled water system and the at least one coil of the air moving unit work in conjunction to cool the air moving within the air moving unit.

Figure 9A:
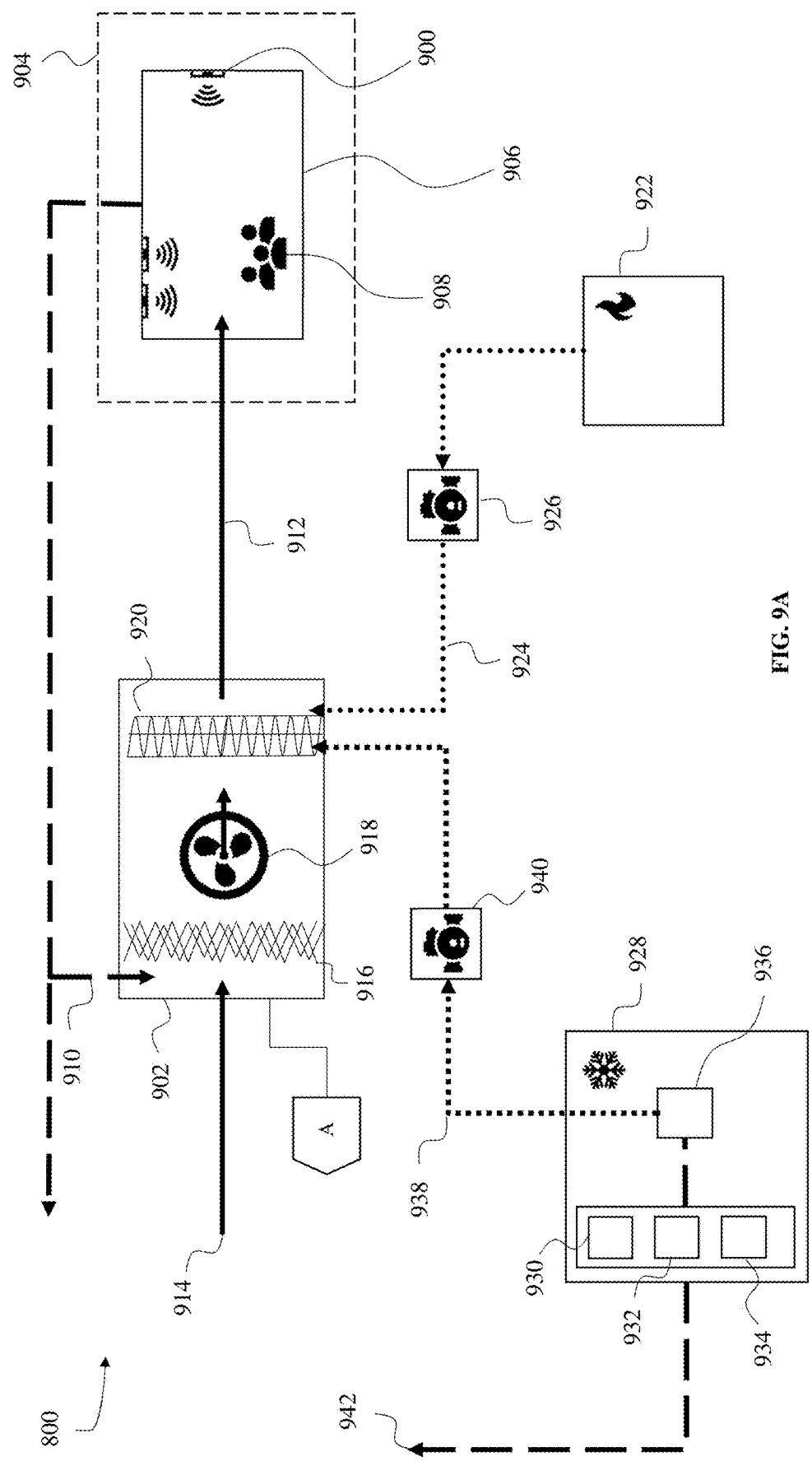
FIG. 9A is a diagram further illustrating the components of the system including the flow of air and water within the system, according to an example embodiment.

Referring now to FIG. 9A, a diagram further illustrating the components of the system 800 including the flow of air and water within the system is shown, according to an example embodiment. The system may further include at least one sensor 900 in operative communication with an air moving unit 902. Operative communication means that the if the sensor detects an operational parameter exceeding its respective predetermined threshold level, then the processor may configure the system to perform at least one of the flushing step, diluting step, and and/or cycling step as described herein. In other embodiments, the processor may engage the system to perform various methods and steps as described herein until the overall net condition of the compartment and/or the enclosed area is within a safe range. The safe range is where people inside the enclosed area have a reduced risk of exposure to contaminants. The sensor is configured to measure operative parameters such as particle count, temperature, and humidity within the enclosed area 904. As illustrated, the enclosed area has at least one ventilated room 906 where the at least one sensor is positioned within the at least one ventilated room. In other embodiments, a plurality of sensors may be positioned within the at least one ventilated room. In some embodiments, the at least one ventilated room may be occupied by beings 908. Beings may include one person one person or a plurality of persons. The at least one ventilated room includes a return air duct 910, as indicated by the bolded dashed arrow, operatively connected to the air moving unit. The return air duct may also comprise an exhaust to allow existing air from within the enclosed room to escape to the outside. In certain embodiments, the exhaust may be configured, via a valve and/or gate, to only allow air to escape through the exhaust when the system is flushing, diluting, and/or cycling. The direction of the bolded dashed arrow indicates the direction of moving air consistent with this disclosure where moving air is removed from the enclosed area. The system further includes a supply air duct 912 operatively connected to the at least one ventilated room, as indicated by the solid bolded arrow. The direction of the solid bolded arrow indicates the direction of the air moving into the enclosed area from the air moving unit where the air is introduced within the enclosed area consistent with this disclosure.

The air moving unit receiving air where the air is at least one of outside air 914 and air from the return air duct which then passes through a filter 916 of the air moving unit. Once the air passes through the filter, the blower 918 of the air moving unit moves the air over the at least one coil 920 of the air moving unit. The at least one coil is operatively connected to a boiler 922 using tubing 924 where a first pump 926 moves heated liquid into the at least one coil. The heated liquid passes through the at least one coil where the at least one coil is configured to raise the temperature of the air moving through the system.

In another embodiment, the at least one coil may be operatively connected to a cooling source 928 where such cooling source, according to an example embodiment, may be a cooling tower. As illustrated, the cooling source having a compressor 930, a condenser coil 932, a fan 934, a chiller 936, and refrigerant filled tubing 938. The cooling source is operatively connected to the air moving unit using the refrigerant filled tubing where cooled or chilled liquid, including refrigerant or chilled water, moves through the refrigerant filled tubing using a second pump 940. The refrigerant or the chilled water passes through the at least one coil where the at least one coil is configured to lower the temperature of the air moving through the system. The fan is configured to move evaporation 942 from the cooling source.

Figure 9B:
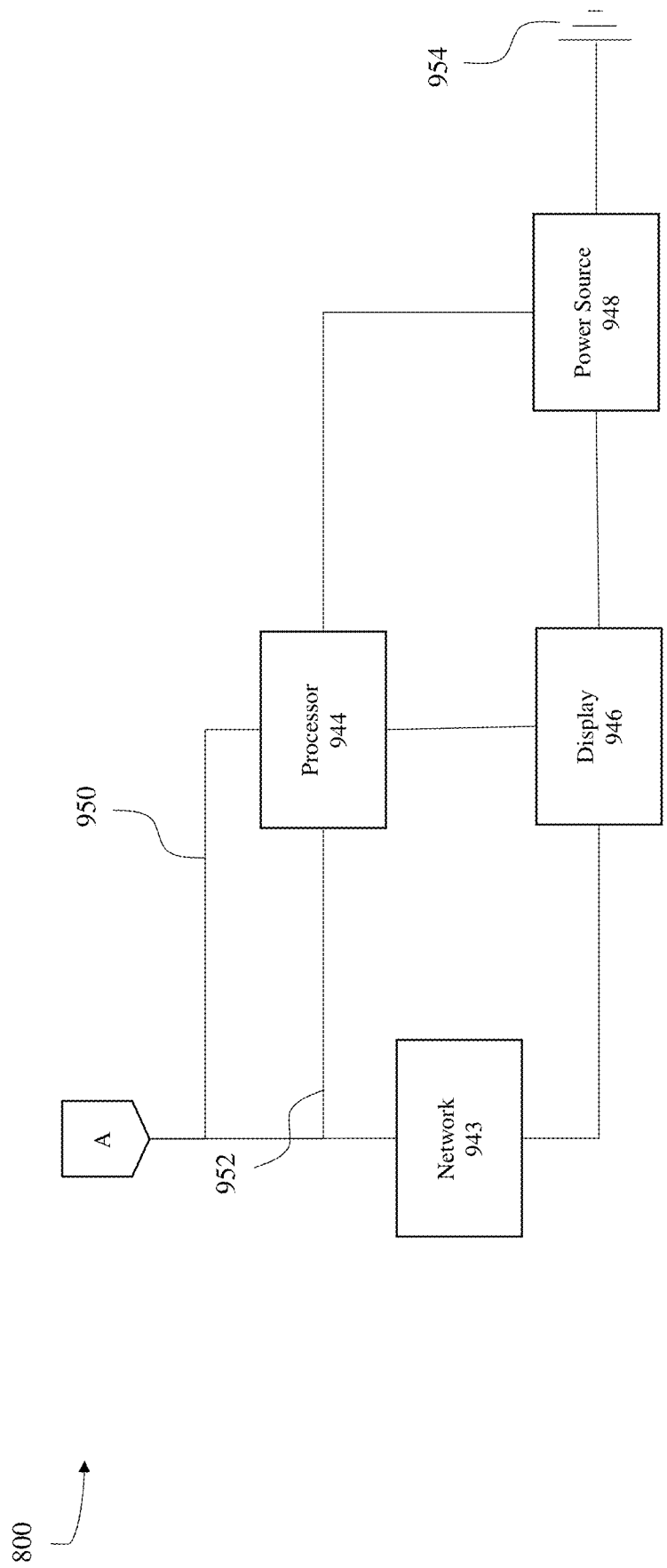
FIG. 9B is a diagram illustrating the system having a display and a processor, according to an example embodiment.

In another embodiment, the system may further include connector A. Referring now to FIG. 9B, a diagram illustrating the system having a display and a processor is shown, according to an example embodiment. The system 800 of FIG. 9A may further include connector A where the system may further include a network 943, a processor 944, a display 946, and a power source 948. The processor 944 may be configured for receiving a first signal 950 and transmit or send a second signal 952. The first signal is received from the system where it contains information from the sensors providing the characteristics of the enclosed area. The second signal, transmitted by the processor, where sending the second signal changes the operational parameters of the system where the system can perform the steps of method 100 including, for example, flushing, filtering, and diluting. The display of the system is in communication with the air moving unit where it may, according to an example embodiment, be connected to a network. The network and the processor may communicate with the display, the information pertaining to a plurality of sensors within the enclosed area. The display may be connected to the network wirelessly or a wired connection. The display is configured for displaying the characteristics of the enclosed area as received from the processor. The system may further be connected to a power source where such power source is configured to supply power to the system, including the display, processor, and other electrical components. The power source may include utility power for example. The power source may further be connected to a ground 954.

Figure 10:
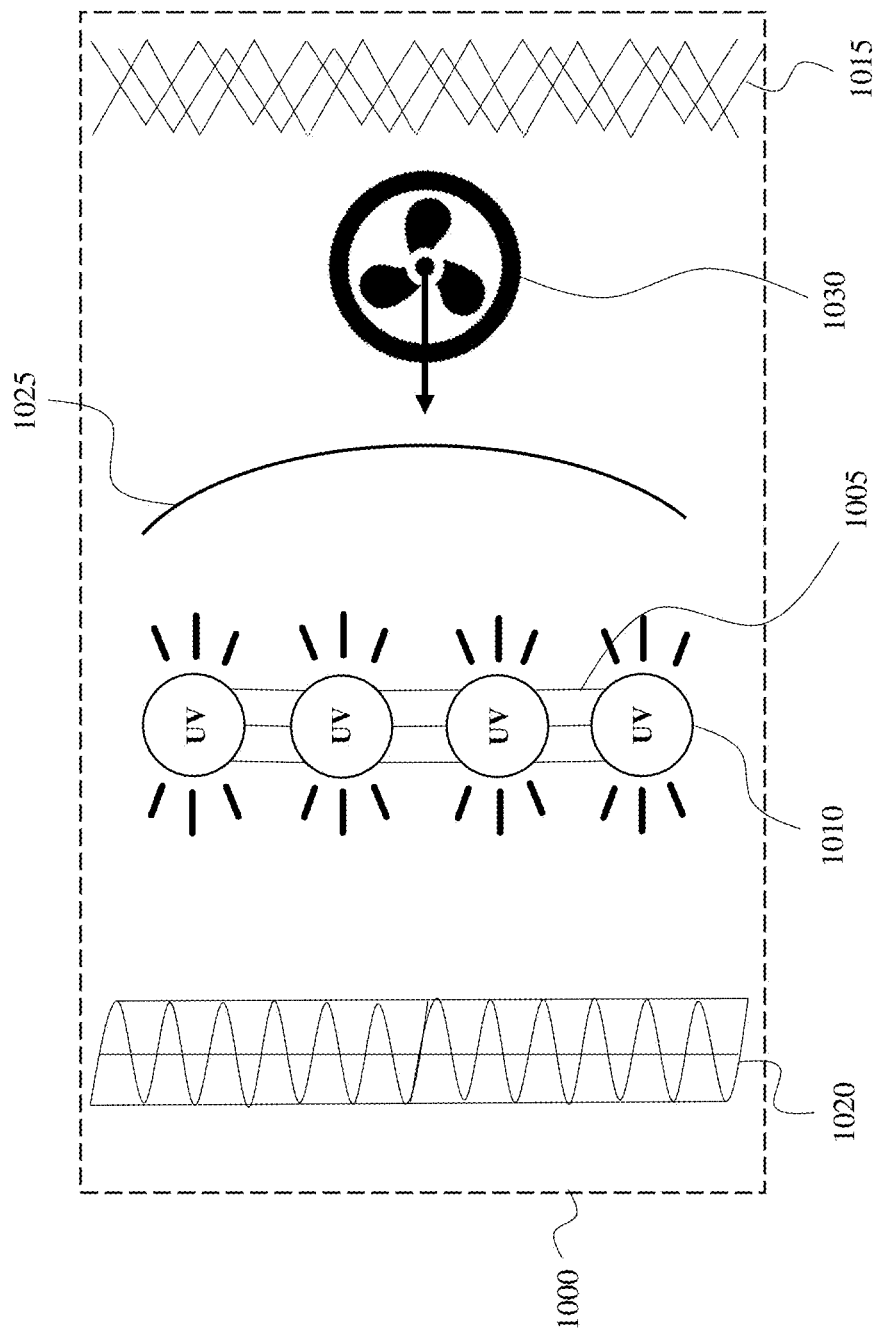
FIG. 10 is a diagram illustrating an air moving unit having a UV infection rack, according to an example embodiment.

Referring now to FIG. 10, a diagram illustrating an air moving unit 1000 having at least one UV infection rack 1005 is shown, according to an example embodiment. The at least one UV infection rack having a plurality of ultraviolet lights removably attached to the UV infection rack where an ultraviolet light can be replaced if damaged or defective. The UV infection rack is configured to removably attach to at least one of the return air duct, the supply air duct, and the air moving unit. In one embodiment, the UV infection rack is configured to removably attach within the air moving unit where the UV infection rack is between a filter 1015 and the at least one coil 1020 where the UV infection rack is oriented to direct ultraviolet waves towards the coil. In another embodiment, the UV infection rack includes a shield 1025, where the shield is oriented between the UV infection rack and the filter, and a blower 1030. The shield is configured to protect the filter and blower from ultraviolet waves that may damage electronic equipment and cause deterioration to the elements of the system. The UV infection rack is configured to removably attach where it can be retrofitted into existing air moving units. The UV infection rack may be removably attached using magnets, for example, where the UV infection rack is magnetically attracted to the surface of the air moving unit. The UV infection rack includes a plurality of ultraviolet lights to increase the contact time with the moving air. The UV infection racks is oriented towards the at least one coil such that the ultraviolet waves destroyed and deactivate microcontaminants on the at least one coil during the UV germicidal irradiation.

Figure 11A:
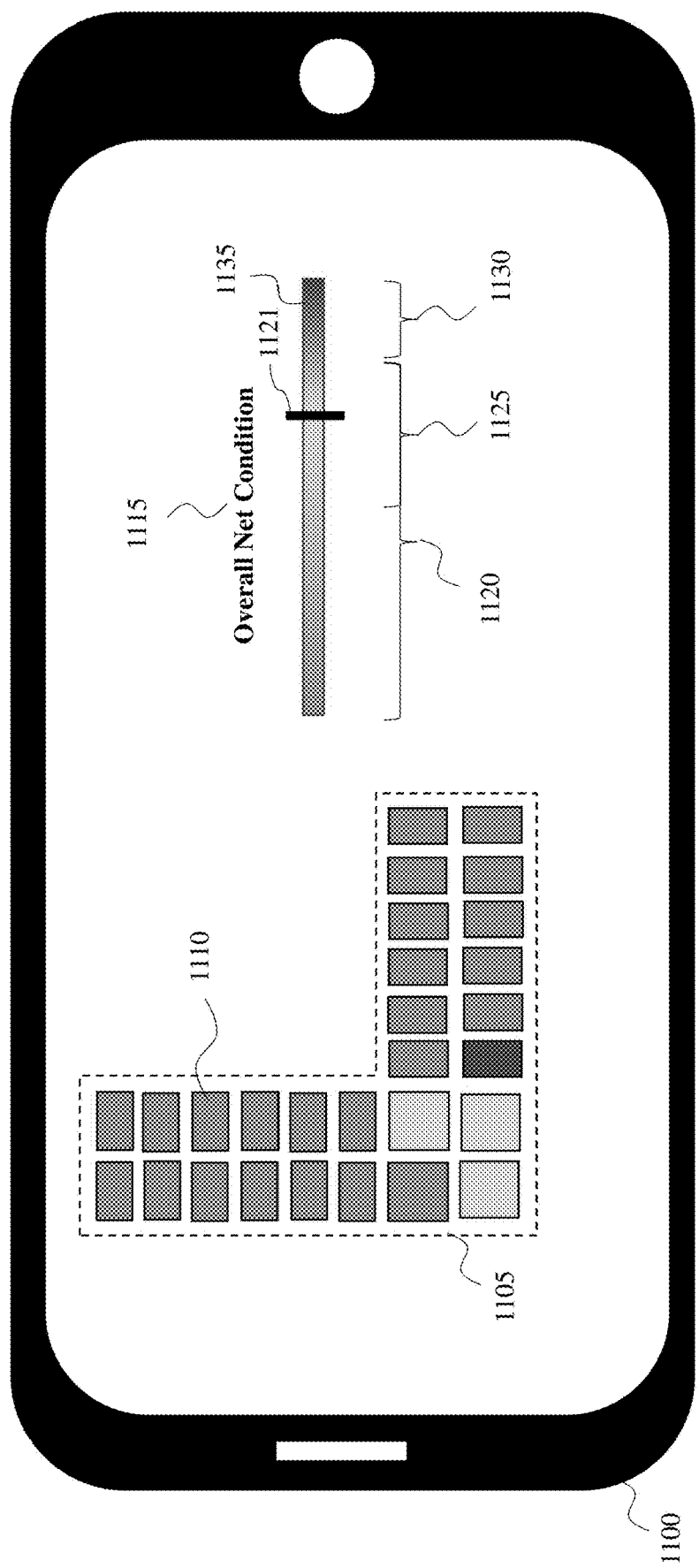
FIG. 11A is a display illustrating whether the characteristics of the enclosed area are maintained within specified limits displaying the overall net conditions of the enclosed area and a graphical depiction of the enclosed area, according to an example embodiment.

Referring now to FIG. 11A, a display illustrating whether the characteristics of the enclosed area are maintained within specified limits displaying the overall net conditions of the enclosed area and a graphical depiction of the enclosed area is shown, according to an example embodiment. The display includes displays configured to provide a graphical depiction of characteristics of an enclosed area. As illustrated, the display 1100 providing a visual representation of the enclosed area 1105 having at least one ventilated room 1110. The enclosed area may be depicted, for example, as a blueprint of a building having a plurality of ventilated rooms, as shown in FIG. 11. The display may further include a fourth indicator 1115 illustrating the overall net condition of the enclosed area as within an overall range 1135. The overall range is predetermined based upon the characteristics of the enclosed area as monitored by the plurality of sensors. In other embodiments, the fourth indicator may display the overall net condition of a specific ventilated room within the enclosed area. The overall net condition 1121 being within a safe range 1120 that is less than the overall net condition predetermined threshold where the safe range includes a green indicator where the enclosed area is within the safe range 1120, a yellow indicator where the enclosed area is approaching the upper limits 1125 of the overall net condition predetermined threshold, and a red indicator where the enclosed area exceeds the upper limits 1130 of the overall net condition predetermined threshold. The overall range 1135 may be represented by a spectrum that starts (from left to right) with the green indicator, transitions into the yellow indicator, and transitions into the red indicator. The overall net condition depends on whether the levels of particulate count, humidity, and temperature are less the respective predetermined thresholds. More specifically, if each of the parameters have not exceeded and not approaching their respective predetermined thresholds, the overall net condition may be within the green indicator of the spectrum. If each of the parameters have not exceeded their predetermined thresholds, but at least one of the parameters are approaching their predetermined threshold, the overall net condition may be within the yellow indicator of the spectrum. Fewer parameters approaching their predetermined threshold may place the overall net condition closer to the yellow-green part of the spectrum while more parameters approaching their predetermined threshold may place the overall net condition closer to the yellow-red part of the spectrum. If at least one parameter has exceeded their predetermined threshold, the overall net condition may be within the red indicator of the spectrum. More parameters exceeding their predetermined thresholds may place the overall net condition deeper in the red indicator of the spectrum.

In other embodiments, each operational parameter may be given a weight in determining the overall net condition of the enclosed area and/or the compartment. For example, a particulate count above the predetermined threshold may turn the system into an unsafe threshold as indicated by a red indicator in the upper limits of the overall net condition. Similarly, temperature and humidity may provide less weight to determining the overall net condition. For example, humidity above the predetermined threshold, such as above 60% may trigger the overall net condition of the enclosed area to approach the upper limits of the safe range, as indicated by a yellow indicator. Other weights of the operational parameters in determining the overall net condition of the compartment and/or the enclosed area are within the spirit and scope of this disclosure.

Figure 11B:
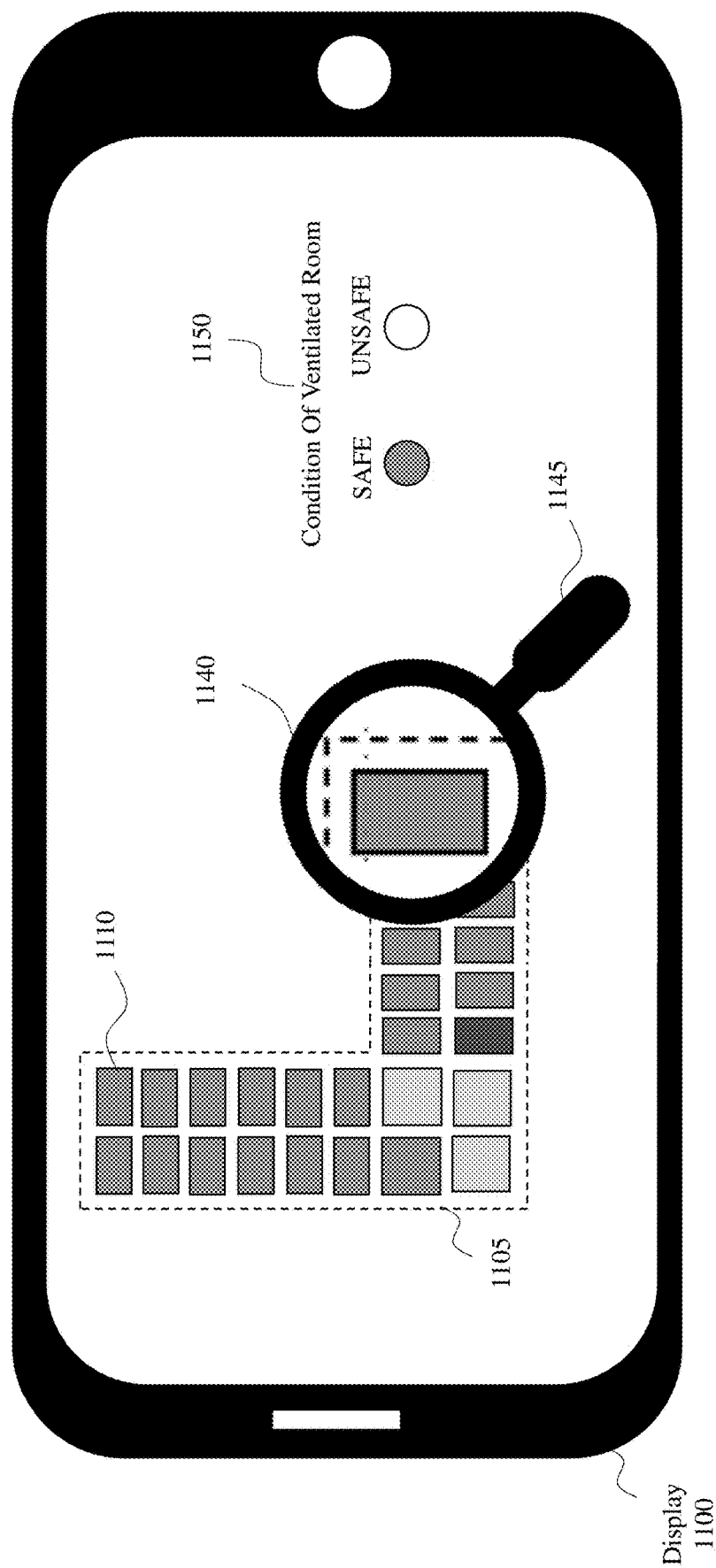
FIG. 11B is a display illustrating whether the characteristics of the at least one ventilated room are in a safe or unsafe condition to a first set of users, such as consumers, according to an example embodiment.

Referring now to FIG. 11B, a display illustrating whether the characteristics of the at least one ventilated room are in a safe or unsafe condition is shown, according to an example embodiment. The enclosed area 1105 includes at least one ventilated room. As displayed, a selecting tool 1145 may be used for selecting a ventilated room 1140. The selecting tool may be a touch indicator where a user may interact with a touch screen to selected at least one ventilated room. The selecting tool may also include a pointer or mouse such that the at least one ventilated room is selected using the click of a computer mouse. In other embodiments, the selecting tool may include a magnifying glass such that selecting the selected ventilated room includes hoovering the selecting tool over the at least one ventilated room. Once the ventilated room is a selected ventilated room 1140, the condition of the selected ventilated room is displayed as a fifth indicator 1150 where the display may include the fifth indicator. The fifth indicator illustrating the condition of the ventilated room may include a safe and unsafe indicator informing the beings that occupy the enclosed area whether the ventilated room is in a safe or unsafe condition. The display of a safe of unsafe condition of a continuously monitored ventilated room reduces the fear beings may associate with unknown hazardous air conditions. The display may continuously display to the beings whether the at least one ventilated room is safe or unsafe the beings. The display is accessible remotely on a remote computing device such as a smart phone or computer application for example.

Figure 11C:
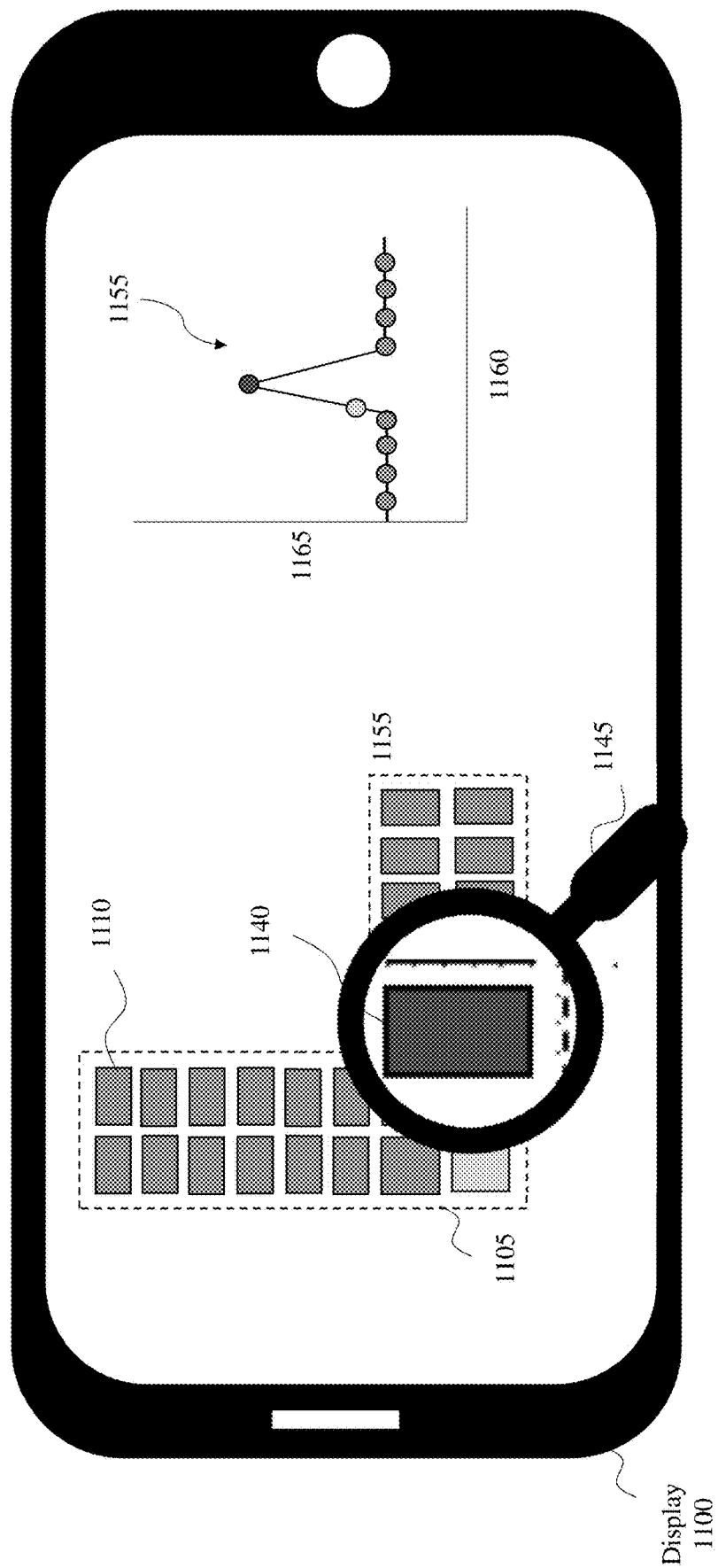
FIG. 11C is a display illustrating the live tracing of the characteristics of the at least one ventilated room, which may be viewable to a second set of users, such as administration or building manages, according to an example embodiment.

Referring now to FIG. 11C, is a display illustrating the live tracing of the characteristics of the at least one ventilated room is shown, according to an example embodiment. This may be used by operations and only be accessible by those with credential and authorization to access the back-end display such as managers and technicians for example. The display may include a live tracing 1155 such that the condition 1165 of the at least one room which is a selected ventilated room, includes past conditions of the ventilated room respective to time 1160. For example, if a selected ventilated room is currently or was in a prior unsafe condition, the back-end user may trace continuously monitored data from the selected ventilated room such that the time, including date and hour for example, can be determined when the selected room became in an unsafe condition. According to one embodiment, the tracing may trace the condition 1165 of the overall condition of the selected ventilated room. In other embodiments, for example, and tracing 1155 may include tracing the condition 1165 of the characteristics of the at least one ventilated room including temperature over time, humidity over time, and particulate count over time for example. The tracing will be able to confirm whether a being was exposed to a ventilated room in an unsafe condition. The tracing will affect insurance and building liability where the system is installed such that claims of unsafe conditions may be determined as factual or false. These interfaces are helpful in allowing users to view the area that they may be using to determine if the location is safe to enter to reduce anxiety and stress.

Figure 12:
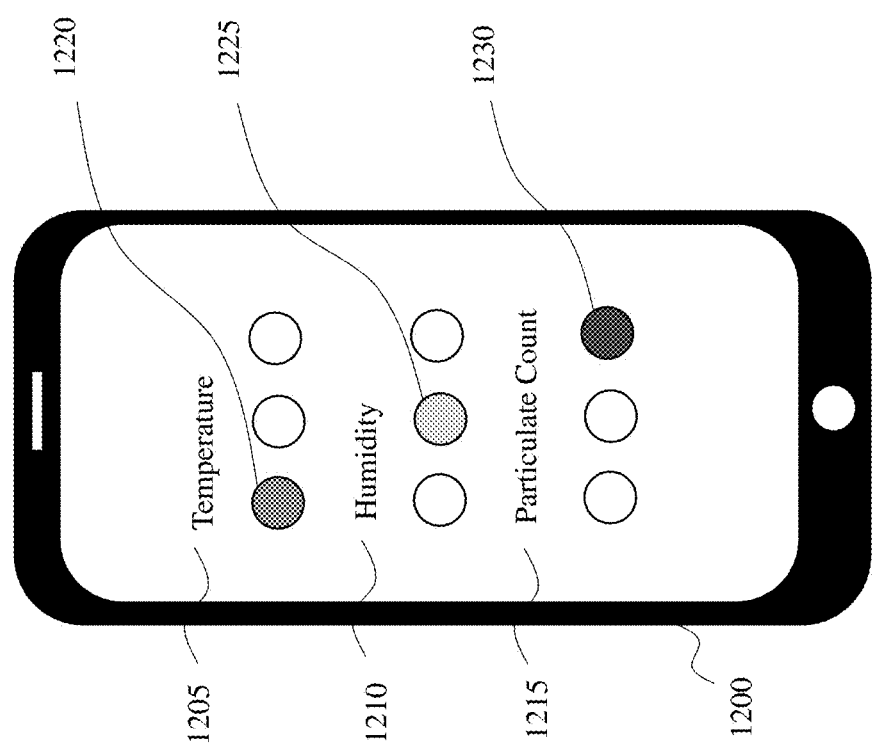
FIG. 12 is a display illustrating whether the characteristics of the enclosed area are maintained within specified limits displaying a first indicator of temperature, a second indicator of humidity, and a third indicator of particulate count, according to an example embodiment.

Referring now to FIG. 12, a display illustrating whether the characteristics of the enclosed area are maintained within specified limits displaying a first indicator of temperature, a second indicator of humidity, and a third indicator of particulate count is shown, according to an example embodiment. The display 1200 having a first indicator 1205 having a particulate count of the enclosed area, where the particulate count within the enclosed area is within a first range; a second indicator 1210 having a temperature of the enclosed area, where the temperature of the enclosed area is within a second range; and a third indicator 1215 having a humidity of the enclosed area, where the humidity of the enclosed area is within a third range. The first indicator, second indicator, and third indicator illustrate the environmental characteristics of the enclosed area as measured by a plurality of sensors. Each of the characteristics of the enclosed area having a predetermined ranger where temperature has a first range, humidity has a second range, and particulate count has a third range. Each of the first, second, and third ranges has a safe range, upper limits of a safe range, and exceeding a safe range where if the measured characteristic is within a safe range, then displaying a green indicator 1220, within the upper limits of the safe range displaying a yellow indicator 1225 and exceeding the upper limits of the safe range displaying a red indicator 1230.

Figure 13:
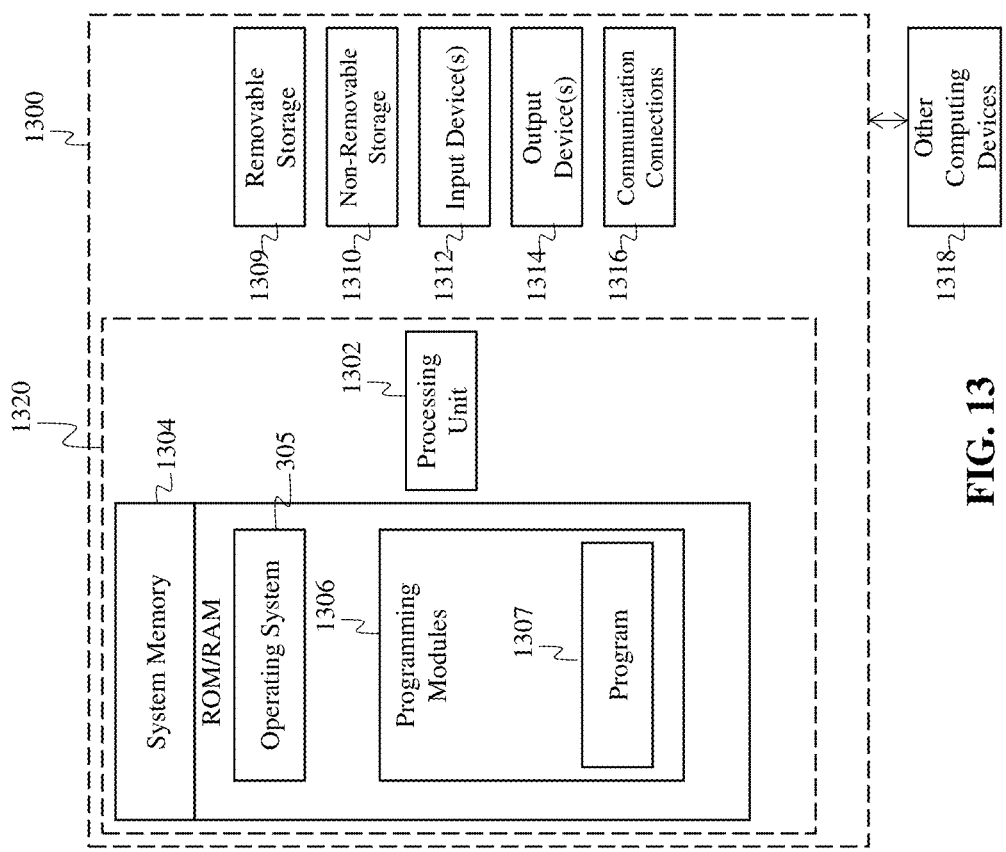
FIG. 13 illustrates a computer system according to exemplary embodiments of the present technology, according to an example embodiment.

Referring now to FIG. 13, a block diagram of a system including an example computing device 1300 and other computing devices. Consistent with the embodiments described herein, the aforementioned actions performed by system 100 may be implemented in a computing device, such as processor 944. Any suitable combination of hardware, software, or firmware may be used to implement processor 944. The aforementioned system, device, and processors are examples and other systems, devices, and processors may comprise the aforementioned computing device. Furthermore, processor 944 may comprise an operating environment for method 100. Processes, data related to method 100 and system 800 may operate in other environments and are not limited to processor 944.

A system consistent with an embodiment of the disclosure may include a plurality of computing devices, such as a computing device 1300 of FIG. 13. In a basic configuration, computing device 1300 may include at least one processing unit 1302 and a system memory 1304. Depending on the configuration and type of computing device, system memory 1304 may comprise, but is not limited to, volatile (e.g., random access memory (RAM)), non-volatile (e.g., read-only memory (ROM)), flash memory, or any combination or memory. System memory 1304 may include operating system 1302, and one or more programming modules 1306. Operating system 1302, for example, may be suitable for controlling computing device 1300's operation. In one embodiment, programming modules 1306 may include, for example, a program module 1307 for executing the actions illustrated in the method 100 of FIG. 1, execute any of the actions of the function of the components illustrated in system 800 of FIG. 9. For example. Furthermore, embodiments of the disclosure may be practiced in conjunction with a graphics library, other operating systems, or any other application program and is not limited to any particular application or system. This basic configuration is illustrated in FIG. 13 by those components within a dashed line 1320.

Computing device 1300 may have additional features or functionality. For example, computing device 1300 may also include additional data storage devices (removable and/or non-removable) such as, for example, magnetic disks, optical disks, or tape. Such additional storage is illustrated in FIG. 13 by a removable storage 1309 and a non-removable storage 1310. Computer storage media may include volatile and nonvolatile, removable, and non-removable media implemented in any method or technology for storage of information, such as computer readable instructions, data structures, program modules, or other data. System memory 1304, removable storage 1309, and non-removable storage 1310 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information, and which can be accessed by computing device 1300. Any such computer storage media may be part of system 1300. Computing device 1300 may also have input device(s) 1312 such as a keyboard, a mouse, a pen, a sound input device, a camera, a touch input device, etc. Output device(s) 1314 such as a display, speakers, a printer, etc. may also be included. The aforementioned devices are only examples, and other devices may be added or substituted.

Computing device 1300 may also contain a communication connection 1316 that may allow system 100 to communicate with other computing devices 1318, such as over a network in a distributed computing environment, for example, an intranet or the Internet. Communication connection 1316 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, several program modules and data files may be stored in system memory 1304, including operating system 1302. While executing on processing unit 1302, programming modules 1306 (e.g., program module 1307) may perform processes including, for example, one or more of the stages of a process. The aforementioned processes are examples, and processing unit 1302 may perform other processes. Other programming modules that may be used in accordance with embodiments of the present disclosure may include electronic mail and contacts applications, word processing applications, spreadsheet applications, database applications, slide presentation applications, drawing or computer-aided application programs, etc.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, multiprocessor systems, microprocessor-based or programmable consumer electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved. It is also understood that components of the system may be interchangeable or modular so that the components may be easily changed or supplemented with additional or alternative components.

While certain embodiments of the disclosure have been described, other embodiments may exist. Furthermore, although embodiments of the present disclosure have been described as associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the disclosure.

Figure 14:
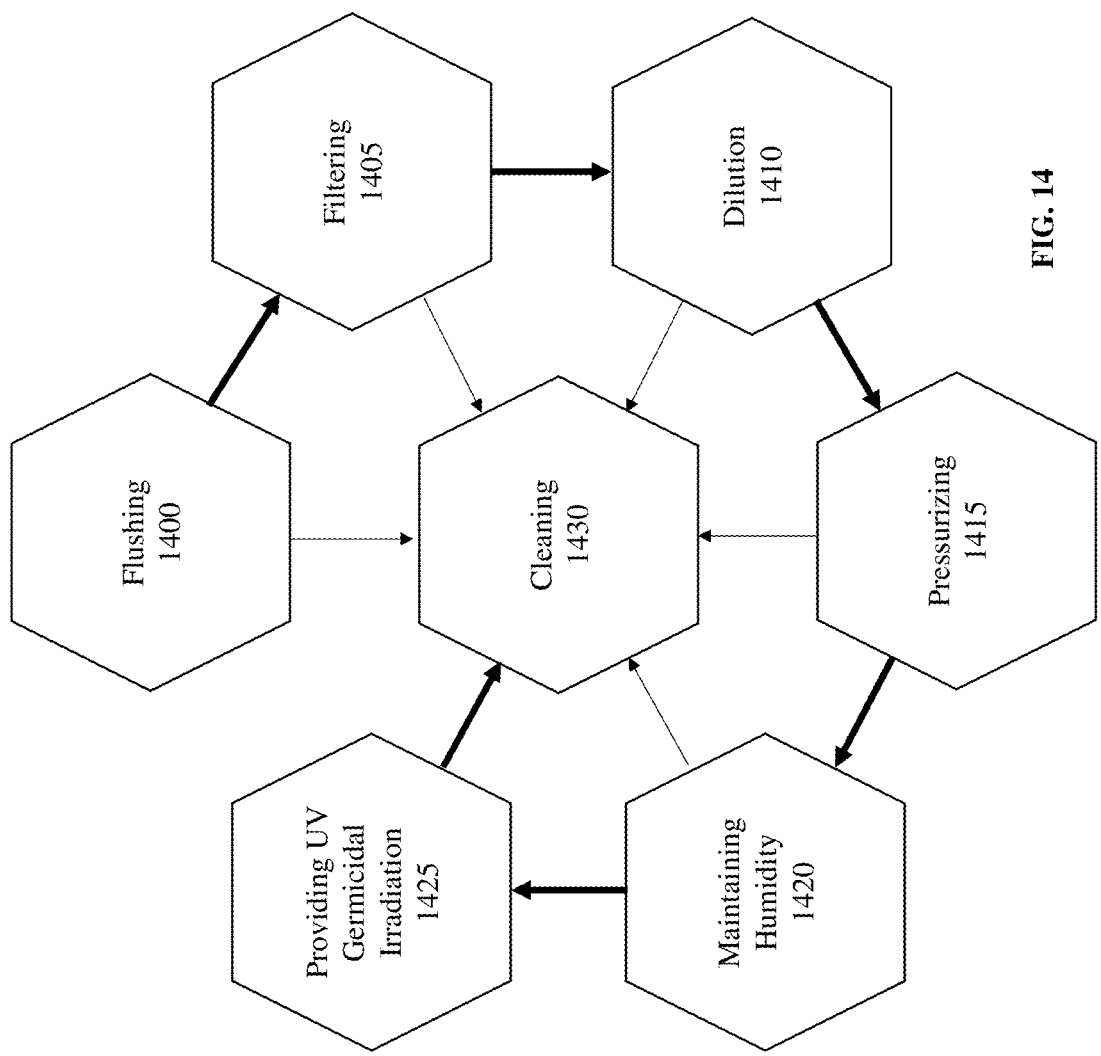
FIG. 14 is a block diagram illustrating a mitigation strategy requiring the sequential application of techniques directed at eliminating, reducing the concentration, and destroying contagions before they can contact building occupants, according to an example embodiment.

Referring now to FIG. 14, a block diagram illustrating a mitigation strategy requiring the sequential application of techniques directed at eliminating, reducing the concentration, and destroying contagions before they can contact building occupants is shown, according to an example embodiment. The strategy incorporates method 100 where the method 100 is a multi-layered system. The multi-layered system is strengthened by built-in redundancy to reduce the number of potential points of failure and incorporates continuous system performance monitoring for timely detection of malfunctions with real-time notification of building occupants as an additional safeguard that enables occupants to respond appropriately if the system does fail. The multilayered system is optimally performed in the order indicated by the bolded arrows, where the method begins with filtering 1400, followed by, filtering 1045, dilution 1410, pressurizing 1415, maintaining humidity 1420, providing germicidal irradiation 1425, and cleaning 1430. The steps of this multi-layered are consistent with this disclosure. As illustrated, each step contributes to the final step of cleaning having synergistic effects on the method and system as a whole. In certain embodiments, dilution step 1410 includes cycling as disclosed herein.

Results

The system and method for mitigating the risk of exposure to contaminants and proving information thereof provided unexpected synergistic effects. The application of the disclosed method improves the mitigation of particles in the room by at least 63% against prior installed air moving units in at least one enclosed area according to testing. Meaning, by providing or using an existing air moving unit, mounting sensors for continuously measuring contaminants, pressure flow, humidity, temperature, and other attributes of the enclosed area; continuously introducing air within the enclosed area using an air moving unit for a specified time prior to and after the enclosed area is occupied by beings; filtering air moving into the enclosed area using at least MERV 14 filters within the air moving unit or return duct; continually introducing air within the enclosed area to allow an increased number of air changes over normal air changes every hour when the enclosed area is occupied by beings; balancing compartments within the enclosed area to either positive, negative, or neutral pressurization for contamination controls; maintaining the humidity within the enclosed area between 40%-60% humidity using the HVAC system; providing UV/sanitization lights mounted to a UV infection rack within at least one of a return air duct, a supply air duct, and the air moving unit for deactivating contaminants from air moving into the enclosed area; cleaning surfaces within the enclosed area based on Global Biorisk Advisory Council (GBAC) standards; adjusting operational parameters of the flushing, filtering, and diluting step above based on (i) reducing energy consumption or (ii) reducing the risk of contaminants within the enclosed area; and providing a display illustrating whether the operational parameters of the enclosed area are maintained within specified limits, a beings risk of exposure to contaminants was mitigated by at least sixty three percent (63%) within the enclosed area. A sixty three percent (63%) mitigation of risk was achieved by flushing for a duration of at least one hour, filtering using at least a MERV-14 filter, and diluting the enclosed area at least 2 air changes per hour, specifically, 2.27 air changes per hour of total air volume of the enclosed area or approximately 4,300 cubic feet per minute. Ultraviolet germicidal irradiation was performed within the air moving unit such that a plurality of ultraviolet lights, specifically two ultraviolet lights were attached within the air moving unit using magnets and directed to expose the at least one coil within the air moving unit to ultraviolet waves.

A test was conducted on the existing air moving unit within the enclosed area. The existing air moving unit was equipped with a MERV-8 filter and no ultraviolet light within the air moving unit. The air moving unit was only capable of introducing outside air at 1,660 cubic feet per minute without overloading the air moving unit. Therefore, the methods and systems disclosed herein provide synergistic effects to mitigating the risk of exposure to contaminants within an enclosed area. The disclosure improves upon current systems by decreasing the risk of exposure to contaminants such that the system was able to decrease at least 63% of contaminants from the air. These results conclude that the use and implementation of the methods and systems herein are applicable to providing safer conditions within enclosed areas and further decreasing the fear people may have while being in an enclosed area knowing they have mitigated risk to exposure of contaminants.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

I claim:

1. A method for controlling air quality in an enclosed area of a plurality of enclosed areas within a building using an HVAC system to mitigate the risk of exposure to airborne contaminants, the method comprising:

mounting a plurality of sensors within each enclosed area of the plurality of enclosed areas, wherein the plurality of sensors within each enclosed area comprises:

a particulate matter sensor configured to measure a relative particulate count in the air within the enclosed area;
a humidity sensor configured to measure a relative humidity within the enclosed area;
a temperature sensor configured to measure a relative temperature within the enclosed area;
wherein the plurality of sensors are configured to continuously measure a parameter value for each of a plurality of operational parameters of the enclosed area;

disposing a first air filter within an air moving unit;
disposing a second air filter in a return duct that is in fluid communication with the enclosed area;
disposing an ultraviolet light within the air moving unit;
assigning a relative weight for each operational parameter of the plurality of operational parameters that are continuously measured in each enclosed area;
calculating an overall net condition of each enclosed area of the plurality of enclosed areas based on the relative weight;
determining, based on the overall net condition, if an operational parameter of the plurality of operational parameters fails to satisfy a predetermined threshold;
wherein the plurality of operational parameters is the relative particulate count, the relative humidity, and the relative temperature;
wherein the predetermined threshold comprises a maximum particulate count threshold, a maximum temperature threshold, a minimum temperature threshold, a maximum humidity threshold, a minimum humidity threshold, and a maximum overall net condition;
if an operational parameter fails to satisfy the predetermined threshold, then determining that the enclosed area is undergoing a triggering event and then:
continuously introducing supply air within the enclosed area using the air moving unit for a specified amount of time after the triggering event;
diluting the supply air within the enclosed area by continuously introducing an increased amount of outside air over a normal amount of outside air into the enclosed area;
flushing the air within the enclosed area by continuously introducing a second amount of supply air within the enclosed area using the air moving unit for a second specified time prior to and after the triggering event;
cycling the supply air within the enclosed area to provide an increased amount of air changes over a normal amount of air changes every hour during the triggering event;
balancing an air pressure of the enclosed area, wherein balancing the air pressure within the enclosed area comprises configuring the enclosed area to be negatively pressurized, such that, upon opening a door to the enclosed area, air flows inward and contaminants within the enclosed area are prevented from exiting; and displaying an indication of the overall net condition of the enclosed area, wherein the indication specifies whether the overall net condition is in a safe state or an unsafe state.

2. The method of claim 1, wherein the indication further comprises:
a first indicator indicating a particulate count of the enclosed area relative to a particulate count predetermined threshold;
a second indicator indicating a temperature of the enclosed area relative to a temperature predetermined threshold;
a third indicator indicating a humidity level of the enclosed area relative to a humidity predetermined threshold; and
a fourth indicator illustrating an overall net condition of the enclosed area relative to an overall net condition predetermined threshold.

3. The method of claim 1, wherein displaying the indication further comprises: providing an overview of the overall net conditions of the plurality of enclosed areas, including the enclosed area and at least one second enclosed area, and displaying an indication of the overall net condition of the enclosed area relative to at least one second indication of the overall net condition of the at least one second enclosed area, wherein the indication of the overall net condition of the enclosed area is at least one of:
a green indicator indicating that the enclosed area is below at least one of the particulate count predetermined threshold, the temperature predetermined threshold, the humidity predetermined threshold, and the overall net condition predetermined threshold;
a yellow indicator where the enclosed area is proximate to an upper limit of at least one of the particulate count predetermined threshold, the temperature predetermined threshold, the humidity predetermined threshold, and the overall net condition predetermined threshold; and
a red indicator where that the enclosed area exceeds the upper limit of at least one of the particulate count predetermined threshold, the temperature predetermined threshold, the humidity predetermined threshold, and the overall net condition predetermined threshold.

* * * * *